(12) United States Patent
Olsen

(10) Patent No.: US 12,702,578 B2
(45) Date of Patent: Aug. 11, 2026

(54) LIQUID SENSING IN OSTOMY APPLIANCE

(71) Applicant: Coloplast A/S, Humlebaek (DK)

(72) Inventor: Jesper Kenneth Olsen, Birkeroed (DK)

(73) Assignee: Coloplast A/S, Humlebaek (DK)

(*) Notice: Subject to any disclaimer, the term of this patent is extended or adjusted under 35 U.S.C. 154(b) by 367 days.

(21) Appl. No.: 18/284,862

(22) PCT Filed: Mar. 29, 2022

(86) PCT No.: PCT/DK2022/050064
§ 371 (c)(1),
(2) Date: Sep. 29, 2023

(87) PCT Pub. No.: WO2022/207049
PCT Pub. Date: Oct. 6, 2022

(65) Prior Publication Data

US 2024/0180736 A1 Jun. 6, 2024

(30) Foreign Application Priority Data

Mar. 29, 2021 (DK) ........................... PA 2021 70152

(51) Int. Cl.
*A61F 5/44* (2006.01)
*A61F 5/443* (2006.01)

(52) U.S. Cl.
CPC ............ *A61F 5/4404* (2013.01); *A61F 5/443* (2013.01)

(58) Field of Classification Search
CPC ............................... A61F 5/4404; A61F 5/445
See application file for complete search history.

(56) References Cited

U.S. PATENT DOCUMENTS 2,054,535 A 9/1936 Diack
2,327,514 A 8/1943 Fenwick
2,542,233 A 2/1951 Carroll
2,544,579 A 3/1951 Ardner
3,214,502 A 10/1965 Schaar
3,808,354 A 4/1974 Feezor et al.
3,832,510 A 8/1974 Pfau et al.
3,915,171 A 10/1975 Shermeta
(Continued)

FOREIGN PATENT DOCUMENTS

CA 2540756 C 1/2008
CA 3009449 C 9/2019
(Continued)

*Primary Examiner* — Susan S Su
*Assistant Examiner* — Erin A Kim
(74) *Attorney, Agent, or Firm* — Coloplast Corp., Coloplast A/S; Nick Baumann

(57) ABSTRACT

An ostomy system comprising a monitor device and an ostomy appliance is disclosed, the ostomy appliance comprising a sensor assembly comprising three or more electrodes including a first, second and third electrode. The first electrode and the second electrode form a primary sensor, and the first electrode and the third electrode form a secondary sensor. The monitor device is configured to determine a first value of an electrical quantity of the primary sensor, to determine a second value of the electrical quantity of the secondary sensor, and to determine an operating state of the ostomy appliance based on at least the absolute difference between the first value and the second value. Also disclosed is a corresponding method and a monitor device.

20 Claims, 5 Drawing Sheets

(56) References Cited

U.S. PATENT DOCUMENTS 3,941,133 A 3/1976 Chen
4,231,369 A 11/1980 Sorensen et al.
4,372,308 A 2/1983 Steer et al.
4,449,970 A 5/1984 Bevan et al.
4,668,227 A 5/1987 Kay
4,754,264 A 6/1988 Okada et al.
4,775,374 A 10/1988 Cilento et al.
4,834,731 A 5/1989 Nowak et al.
4,973,323 A 11/1990 Kaczmarek et al.
4,982,742 A 1/1991 Claude
5,013,307 A 5/1991 Broida
5,016,645 A 5/1991 Williams et al.
5,051,259 A 9/1991 Olsen et al.
5,074,851 A 12/1991 Plass et al.
5,111,812 A 5/1992 Swanson et al.
5,167,650 A 12/1992 Johnsen et al.
5,197,895 A 3/1993 Stupecky
5,237,995 A 8/1993 Cano
5,318,543 A 6/1994 Ross et al.
5,358,488 A 10/1994 Suriyapa
5,486,158 A 1/1996 Samuelsen
5,519,644 A 5/1996 Benton
5,570,082 A 10/1996 Mahgerefteh et al.
5,593,397 A 1/1997 La Gro
5,672,163 A 9/1997 Ferreira et al.
5,677,221 A 10/1997 Tseng
5,704,905 A 1/1998 Jensen et al.
5,790,036 A 8/1998 Fisher et al.
5,800,415 A 9/1998 Olsen
5,816,252 A 10/1998 Faries, Jr. et al.
5,834,009 A 11/1998 Sawers et al.
5,846,558 A 12/1998 Nielsen et al.
5,876,855 A 3/1999 Wong et al.
5,879,292 A 3/1999 Sternberg et al.
5,942,186 A 8/1999 Sanada et al.
6,015,399 A 1/2000 Mracna et al.
6,025,725 A 2/2000 Gershenfeld et al.
6,057,689 A 5/2000 Saadat
6,078,261 A 6/2000 Davsko
6,103,033 A 8/2000 Say et al.
6,135,986 A 10/2000 Leisner et al.
6,165,005 A 12/2000 Mills et al.
6,171,289 B1 1/2001 Millot et al.
6,206,864 B1 3/2001 Kavanagh et al.
6,241,704 B1 6/2001 Peterson et al.
6,246,330 B1 6/2001 Nielsen
6,270,445 B1 8/2001 Dean, Jr. et al.
6,297,422 B1 10/2001 Hansen et al.
6,407,308 B1 6/2002 Roe et al.
6,433,244 B1 8/2002 Roe et al.
6,482,491 B1 11/2002 Samuelsen et al.
6,485,476 B1 11/2002 von Dyck et al.
6,520,943 B1 2/2003 Wagner
6,659,989 B1 12/2003 Otto
6,764,474 B2 7/2004 Nielsen et al.
7,049,478 B1 5/2006 Smith
7,066,919 B1 6/2006 Sauerland et al.
7,150,728 B2 12/2006 Hansen et al.
7,166,091 B1 1/2007 Zeltner
7,199,501 B2 4/2007 Pei et al.
7,214,217 B2 5/2007 Pedersen et al.
7,221,279 B2 5/2007 Nielsen
7,326,190 B2 2/2008 Botten
7,341,578 B2 3/2008 von Bulow et al.
7,347,844 B2 3/2008 Cline et al.
7,367,965 B2 5/2008 Poulsen et al.
7,422,578 B2 9/2008 Shan et al.
7,559,922 B2 7/2009 Botten
7,625,362 B2 12/2009 Boehringer et al.
7,641,612 B1 1/2010 McCall
7,670,289 B1 3/2010 McCall
7,943,812 B2 5/2011 Stroebeck et al.
7,981,098 B2 7/2011 Boehringer et al.
8,061,360 B2 11/2011 Locke et al.
8,277,427 B2 10/2012 Edvardsen et al.
8,319,003 B2 11/2012 Olsen et al.
8,326,051 B1 12/2012 Hobbs
8,398,575 B1 3/2013 McCall
8,398,603 B2 3/2013 Thirstrup et al.
8,399,732 B2 3/2013 Oelund et al.
8,409,158 B2 4/2013 Edvardsen et al.
8,449,471 B2 5/2013 Tran
8,474,338 B2 7/2013 Gelman et al.
8,500,718 B2 8/2013 Locke et al.
8,632,492 B2 1/2014 DeLegge
8,680,991 B2 3/2014 Tran
8,684,982 B2 4/2014 Nguyen-Demary et al.
8,740,865 B2 6/2014 Krystek et al.
8,795,257 B2 8/2014 Coulthard et al.
D712,545 S 9/2014 Igwebuike et al.
8,821,464 B2 9/2014 Hanuka et al.
8,975,465 B2 3/2015 Hong et al.
8,979,813 B2 3/2015 Uveborn
9,046,085 B2 6/2015 Schoess et al.
9,066,812 B2 6/2015 Edvardsen et al.
9,216,104 B2 12/2015 Thirstrup et al.
9,308,332 B2 4/2016 Heppe
9,322,797 B1 4/2016 Lastinger et al.
9,566,383 B2 2/2017 Yodfat et al.
9,629,779 B2 4/2017 Grum-Schwensen et al.
9,629,964 B2 4/2017 Wuepper
9,675,267 B2 6/2017 Laakkonen et al.
9,693,908 B2 7/2017 Eriksson et al.
9,770,359 B2 9/2017 Edvardsen et al.
9,788,991 B2 10/2017 Bird
9,867,934 B2 1/2018 Heppe
9,928,341 B2 3/2018 Angelides
10,016,298 B2 7/2018 Thirstrup et al.
D826,740 S 8/2018 Stevens et al.
10,426,342 B2 10/2019 Hresko et al.
10,500,084 B2 12/2019 Hansen et al.
10,531,977 B2 1/2020 Schoess et al.
10,646,370 B2 5/2020 Keleny et al.
10,792,184 B2 10/2020 Hvid et al.
10,799,385 B2 10/2020 Hansen et al.
10,849,781 B2 12/2020 Hansen et al.
10,874,541 B2 12/2020 Seres et al.
10,987,243 B2 4/2021 Thirstrup et al.
11,096,818 B2 8/2021 Thirstrup et al.
11,135,084 B2 10/2021 Seres et al.
11,238,133 B1 2/2022 Brewer et al.
11,306,224 B2 4/2022 Chatterjee et al.
11,406,525 B2 8/2022 Seres et al.
11,471,318 B2 10/2022 Hansen et al.
11,491,042 B2 11/2022 Seres et al.
11,534,323 B2 12/2022 Hansen et al.
11,540,937 B2 1/2023 Hansen et al.
11,547,595 B2 1/2023 Hansen et al.
11,547,596 B2 1/2023 Hansen et al.
11,559,423 B2 1/2023 Speiermann et al.
11,559,426 B2 1/2023 Sletten et al.
2001/0041920 A1 11/2001 Starkweather et al.
2001/0051787 A1 12/2001 Haller et al.
2002/0013613 A1 1/2002 Haller et al.
2002/0019615 A1 2/2002 Roe et al.
2002/0109621 A1 8/2002 Khair et al.
2003/0132763 A1 7/2003 Ellenz
2003/0169032 A1 9/2003 Minchole et al.
2004/0006320 A1 1/2004 Buglino et al.
2004/0030305 A1 2/2004 Sakamoto
2004/0036484 A1 2/2004 Tamai
2004/0049145 A1 3/2004 Flick
2004/0068244 A1 4/2004 Salone et al.
2004/0078219 A1 4/2004 Kaylor et al.
2004/0100376 A1 5/2004 Lye et al.
2004/0106908 A1 6/2004 Leise, Jr. et al.
2004/0111072 A1 6/2004 McKissick
2004/0133175 A1 7/2004 Hagedorn-Olsen
2004/0171999 A1 9/2004 Andersen et al.
2004/0193122 A1 9/2004 Cline et al.
2004/0193123 A1 9/2004 Fenton
2004/0216833 A1 11/2004 Fleming et al.
2005/0054997 A1 3/2005 Buglino et al.
2005/0065488 A1 3/2005 Elliott

(56) References Cited

U.S. PATENT DOCUMENTS

2005/0070863 A1 3/2005 Bulow et al.
2005/0085779 A1 4/2005 Poulsen et al.
2005/0101841 A9 5/2005 Kaylor et al.
2005/0240163 A1 10/2005 Andersen
2005/0256545 A1 11/2005 Koh et al.
2005/0261645 A1 11/2005 Conrad et al.
2006/0015081 A1 1/2006 Suzuki et al.
2006/0025727 A1 2/2006 Boehringer et al.
2006/0052752 A1 3/2006 McMichael
2006/0194324 A1 8/2006 Faries, Jr. et al.
2006/0271002 A1 11/2006 Botten
2007/0010256 A1 1/2007 Klabunde et al.
2007/0035405 A1 2/2007 Wada et al.
2007/0135782 A1 6/2007 Bager et al.
2007/0185464 A1 8/2007 Fattman et al.
2007/0204691 A1 9/2007 Bogner et al.
2008/0038536 A1 2/2008 Strobech et al.
2008/0041792 A1 2/2008 Crnkovich et al.
2008/0071214 A1 3/2008 Locke et al.
2008/0075934 A1 3/2008 Barlow, Jr. et al.
2008/0091154 A1 4/2008 Botten
2008/0096726 A1 4/2008 Riley et al.
2008/0097360 A1 4/2008 Andersen et al.
2008/0140057 A1 6/2008 Wood et al.
2008/0234641 A1 9/2008 Locke et al.
2008/0275327 A1 11/2008 Faarbaek et al.
2008/0278337 A1 11/2008 Huang et al.
2008/0300559 A1 12/2008 Gustafson et al.
2008/0300578 A1 12/2008 Freedman
2008/0306459 A1 12/2008 Albrectsen
2009/0012501 A1 1/2009 Boehringer et al.
2009/0118600 A1 5/2009 Ortiz et al.
2009/0118687 A1 5/2009 Kristensen et al.
2009/0167286 A1 7/2009 Naylor et al.
2009/0173935 A1 7/2009 Cho et al.
2009/0216169 A1 8/2009 Hansen et al.
2009/0227969 A1 9/2009 Jaeb et al.
2009/0234916 A1 9/2009 Cosentino et al.
2009/0247970 A1 10/2009 Keleny et al.
2009/0264957 A1 10/2009 Giftakis et al.
2010/0010460 A1 1/2010 Butler
2010/0030167 A1 2/2010 Thirstrup et al.
2010/0036206 A1 2/2010 Lorio
2010/0072271 A1 3/2010 Thorstensson
2010/0076275 A1 3/2010 Chu et al.
2010/0106220 A1 4/2010 Ecker et al.
2010/0114047 A1 5/2010 Song et al.
2010/0271212 A1 10/2010 Page
2010/0311167 A1 12/2010 Wood et al.
2011/0034890 A1 2/2011 Stroebech et al.
2011/0077497 A1 3/2011 Oster et al.
2011/0130642 A1 6/2011 Jaeb et al.
2011/0245682 A1 10/2011 Robinson et al.
2011/0246983 A1 10/2011 Brunet et al.
2011/0257496 A1 10/2011 Terashima et al.
2012/0013130 A1 1/2012 Jung
2012/0143154 A1 6/2012 Edvardsen et al.
2012/0143155 A1 6/2012 Edvardsen et al.
2012/0253224 A1 10/2012 Mir et al.
2012/0258302 A1 10/2012 Hunt et al.
2012/0259230 A1 10/2012 Riley
2012/0283678 A1 11/2012 Nguyen-Demary et al.
2012/0304767 A1 12/2012 Howard et al.
2013/0018231 A1 1/2013 Hong et al.
2013/0030167 A1 1/2013 Wang et al.
2013/0030397 A1 1/2013 Sabeti
2013/0060213 A1 3/2013 Hanuka et al.
2013/0066285 A1 3/2013 Locke et al.
2013/0072886 A1 3/2013 Schertiger et al.
2013/0078912 A1 3/2013 San Vicente et al.
2013/0086217 A1 4/2013 Price et al.
2013/0102979 A1 4/2013 Coulthard et al.
2013/0138065 A1 5/2013 Buus
2013/0150769 A1 6/2013 Heppe
2013/0165862 A1 6/2013 Griffith et al.
2013/0192604 A1 8/2013 Persson et al.
2013/0226116 A1 8/2013 Edvardsen et al.
2013/0231620 A1 9/2013 Thirstrup et al.
2013/0261575 A1 10/2013 Kiyoshi
2013/0267790 A1 10/2013 Pfuetzner et al.
2013/0303867 A1 11/2013 Elfstrom et al.
2013/0324952 A1 12/2013 Krystek et al.
2013/0324955 A1 12/2013 Wong et al.
2014/0051946 A1 2/2014 Arne et al.
2014/0128815 A1 5/2014 Cabiri et al.
2014/0200426 A1 7/2014 Taub et al.
2014/0200538 A1 7/2014 Euliano et al.
2014/0236111 A1 8/2014 Casado et al.
2014/0236335 A1 8/2014 Lewis et al.
2014/0275854 A1 9/2014 Venkatraman et al.
2014/0276501 A1 9/2014 Cisko
2014/0288381 A1 9/2014 Faarbaek et al.
2014/0303574 A1 10/2014 Knutson
2014/0309600 A1 10/2014 Aceto et al.
2014/0323909 A1 10/2014 Kim
2014/0327433 A1 11/2014 Anway et al.
2014/0336493 A1 11/2014 Kulach et al.
2015/0057634 A1 2/2015 Mastrototaro et al.
2015/0150457 A1 6/2015 Wu et al.
2015/0151051 A1 6/2015 Tsoukalis
2015/0230706 A1 8/2015 Nakagawa et al.
2015/0231802 A1 8/2015 Quan et al.
2015/0250639 A1 9/2015 Thirstrup et al.
2015/0257923 A1 9/2015 Thirstrup et al.
2015/0328389 A1 11/2015 Heppe
2015/0342777 A1 12/2015 Seres et al.
2015/0351690 A1 12/2015 Toth et al.
2015/0374896 A1 12/2015 Du et al.
2016/0008182 A1 1/2016 Prokopuk et al.
2016/0015570 A1 1/2016 Heinecke et al.
2016/0058604 A1 3/2016 Wiltshire et al.
2016/0084869 A1 3/2016 Yuen et al.
2016/0103966 A1 4/2016 Mirza
2016/0117062 A1 4/2016 Hussam et al.
2016/0158056 A1 6/2016 Davis et al.
2016/0158517 A1 6/2016 Nebbia
2016/0158969 A1 6/2016 McLane et al.
2016/0166438 A1 6/2016 Rovaniemi
2016/0178387 A1 6/2016 Yamasaki et al.
2016/0218555 A1 7/2016 Slaby et al.
2016/0235581 A1 8/2016 Keleny et al.
2016/0242654 A1 8/2016 Quinlan et al.
2016/0278990 A1 9/2016 Chen
2016/0284084 A1 9/2016 Gurcan et al.
2016/0305776 A1 10/2016 Mårtensson et al.
2016/0310077 A1 10/2016 Hunter et al.
2016/0310140 A1 10/2016 Belson et al.
2016/0310329 A1 10/2016 Patel et al.
2016/0317728 A1 11/2016 Lewis et al.
2016/0331232 A1 11/2016 Love et al.
2016/0361015 A1 12/2016 Wang et al.
2017/0042614 A1 2/2017 Salahieh et al.
2017/0050004 A1 2/2017 Tilson et al.
2017/0055896 A1 3/2017 Al-Ali et al.
2017/0079530 A1 3/2017 DiMaio et al.
2017/0079576 A1 3/2017 Stroebech et al.
2017/0098044 A1 4/2017 Lai et al.
2017/0112658 A1 4/2017 Hosono
2017/0113001 A1 4/2017 Trock
2017/0140103 A1 5/2017 Angelides
2017/0156920 A1 6/2017 Hunt et al.
2017/0181628 A1 6/2017 Burnette et al.
2017/0262986 A1 9/2017 Xiong et al.
2017/0319073 A1 11/2017 DiMaio et al.
2017/0340474 A1 11/2017 Thirstrup et al.
2017/0340498 A1 11/2017 Tessmer et al.
2017/0348137 A1 12/2017 Hvid et al.
2017/0360592 A1 12/2017 Carrubba
2017/0360593 A1 12/2017 Cox
2018/0021164 A1 1/2018 Fenton
2018/0021165 A1 1/2018 Fenton
2018/0049667 A1 2/2018 Heppe
2018/0055359 A1 3/2018 Shamim et al.
2018/0078163 A1 3/2018 Welch

(56) References Cited

U.S. PATENT DOCUMENTS

2018/0109852 A1 4/2018 Mandapaka et al.
2018/0110078 A1 4/2018 Mandapaka et al.
2018/0136712 A1 5/2018 Niikura et al.
2018/0171183 A1 6/2018 Sakurai et al.
2018/0177626 A1 6/2018 Israelson
2018/0250156 A1 9/2018 Lam
2018/0298240 A1 10/2018 Chatterjee et al.
2018/0318475 A1 11/2018 Thomson et al.
2018/0344533 A1 12/2018 Rovaniemi
2019/0008439 A1 1/2019 Sageder et al.
2019/0099552 A1 4/2019 Zhang et al.
2019/0133810 A1 5/2019 Seres et al.
2019/0133811 A1 5/2019 Seres et al.
2019/0133812 A1* 5/2019 Seres ...................... A61F 5/443
2019/0142623 A1 5/2019 Schoess et al.
2019/0175386 A1 6/2019 Monty
2019/0184093 A1 6/2019 Sjolund et al.
2019/0192066 A1 6/2019 Schoess et al.
2019/0192332 A1* 6/2019 Hansen ................ A61B 5/7475
2019/0192333 A1 6/2019 Hansen et al.
2019/0192334 A1 6/2019 Hansen et al.
2019/0240059 A1 8/2019 Seres et al.
2019/0247050 A1 8/2019 Goldsmith
2019/0374163 A1 12/2019 Faarbaek et al.
2019/0374372 A1 12/2019 Seres et al.
2020/0100931 A1 4/2020 Schoess et al.
2020/0188161 A1 6/2020 Seres et al.
2020/0246174 A1 8/2020 Hansen et al.
2020/0246175 A1 8/2020 Hansen et al.
2020/0246176 A1 8/2020 Hansen et al.
2020/0246177 A1 8/2020 Hansen et al.
2020/0276063 A1 9/2020 Muñoz Herencia
2020/0279368 A1 9/2020 Tada et al.
2020/0297244 A1 9/2020 Brownhill et al.
2020/0306074 A1 10/2020 Speiermann et al.
2020/0322793 A1 10/2020 Yang
2020/0330258 A1 10/2020 Hansen et al.
2020/0330260 A1 10/2020 Hansen et al.
2020/0337880 A1 10/2020 Hansen et al.
2020/0337881 A1 10/2020 Hansen et al.
2020/0337882 A1 10/2020 Hansen et al.
2020/0337883 A1 10/2020 Hansen et al.
2020/0375499 A1 12/2020 Hansen et al.
2020/0375782 A1 12/2020 Hansen et al.
2020/0375783 A1 12/2020 Hansen et al.
2020/0375784 A1 12/2020 Hansen et al.
2020/0375785 A1 12/2020 Hansen et al.
2020/0375786 A1 12/2020 Hansen et al.
2020/0375809 A1 12/2020 Sullivan et al.
2020/0383637 A1 12/2020 Hansen et al.
2020/0383818 A1 12/2020 Hansen et al.
2020/0383819 A1 12/2020 Sletten et al.
2020/0383820 A1 12/2020 Hansen et al.
2020/0383821 A1 12/2020 Hansen et al.
2020/0390587 A1 12/2020 Svanegaard et al.
2020/0390588 A1 12/2020 Hansen et al.
2020/0390589 A1 12/2020 Hansen et al.
2020/0395120 A1 12/2020 Svanegaard et al.
2020/0395610 A1 12/2020 Ono et al.
2020/0405228 A1 12/2020 Svanegaard et al.
2020/0405229 A1 12/2020 Svanegaard et al.
2020/0405230 A1 12/2020 Svanegaard et al.
2021/0000414 A1 1/2021 Svanegaard et al.
2021/0000633 A1 1/2021 Hansen et al.
2021/0000634 A1 1/2021 Svanegaard et al.
2021/0000635 A1 1/2021 Hansen et al.
2021/0000636 A1 1/2021 Hansen et al.
2021/0007663 A1 1/2021 Svanegaard et al.
2021/0007881 A1 1/2021 Svanegaard et al.
2021/0015653 A1 1/2021 Hansen et al.
2021/0015654 A1 1/2021 Hansen et al.
2021/0022683 A1 1/2021 Faarbaek et al.
2021/0038424 A1 2/2021 Svanegaard et al.
2021/0059603 A1 3/2021 Svanegaard et al.
2021/0085511 A1 3/2021 Hansen et al.
2021/0085512 A1 3/2021 Hansen et al.
2021/0100533 A1 4/2021 Seres et al.
2021/0128364 A1 5/2021 Cole et al.
2021/0177642 A1 6/2021 Andersen et al.
2021/0212855 A1 7/2021 Hansen et al.
2021/0228194 A1 7/2021 Mayberg
2021/0338471 A1 11/2021 Nolan et al.
2021/0361464 A1 11/2021 Larsen et al.
2021/0361465 A1 11/2021 Hansen et al.
2021/0361466 A1 11/2021 Hansen et al.
2021/0361467 A1 11/2021 Hansen et al.
2021/0369197 A1 12/2021 Hansen et al.
2021/0369488 A1 12/2021 Hansen et al.
2021/0369489 A1 12/2021 Hansen et al.
2021/0369490 A1 12/2021 Hansen et al.
2021/0370217 A1 12/2021 Kirschman
2021/0386368 A1 12/2021 Carlsson et al.
2022/0000652 A1 1/2022 Thirstrup et al.
2022/0031227 A1 2/2022 Cho et al.
2022/0031495 A1 2/2022 Seres et al.
2022/0079802 A1 3/2022 Hansen
2022/0079803 A1 3/2022 Windeballe et al.
2022/0087851 A1 3/2022 Stroebech
2022/0110585 A1 4/2022 Andersen
2022/0117771 A1 4/2022 Fearn et al.
2022/0142807 A1 5/2022 Tofte
2022/0192860 A1 6/2022 Hansen et al.
2022/0241104 A1 8/2022 Knoedler
2022/0241105 A1 8/2022 Hansen et al.
2022/0265458 A1 8/2022 Carlsson et al.
2022/0378602 A1 12/2022 Hansen et al.
2023/0059470 A1 2/2023 Hansen et al.
2023/0064734 A1 3/2023 Hansen et al.
2023/0105402 A1 4/2023 Hansen et al.
2023/0117727 A1 4/2023 Hansen et al.
2023/0118594 A1 4/2023 Speiermann et al.
2023/0145670 A1 5/2023 Seres et al.
2023/0190509 A1 6/2023 Hansen et al.
2023/0210682 A1 7/2023 Hansen et al.
2023/0233147 A1 7/2023 Hansen et al.
2023/0329893 A1 10/2023 Olsen et al.
2023/0338005 A1 10/2023 Barthe et al.

FOREIGN PATENT DOCUMENTS

CA 3002372 C 3/2021
CA 2947016 C 2/2023
CN 203786580 U 8/2014
CN 104902399 A 9/2015
CN 104980878 A 10/2015
CN 105588856 A 5/2016
CN 206271160 U 6/2017
CN 206450708 U 8/2017
CN 107661167 A 2/2018
CN 105615896 B 5/2019
CN 105359167 B 6/2019
DE 3437950 A1 4/1985
DE 3836590 A1 5/1990
DE 19900611 C1 7/2000
DE 69722993 7/2003
DE 102011014321 A1 9/2012
DE 102011076219 A1 11/2012
EP 0168967 A1 1/1986
EP 0373782 B1 10/1994
EP 0416397 B1 5/1995
EP 0800804 B1 6/2003
EP 1188157 B1 12/2005
EP 2108345 A1 10/2009
EP 1275357 B1 3/2011
EP 2000083 B1 8/2012
EP 2601915 A1 6/2013
EP 2738960 A1 6/2014
EP 2489561 B1 8/2014
EP 2453851 B1 10/2014
EP 2654646 B1 7/2016
EP 3213727 B1 12/2019
EP 3064179 B1 9/2021
EP 3226946 B1 8/2023
GB 2219679 A 12/1989

(56) References Cited

FOREIGN PATENT DOCUMENTS

| | | | |
|---|---|---|---|
| GB | 2308306 | B | 9/1999 |
| GB | 2343628 | B | 10/2000 |
| GB | 2465742 | B | 7/2012 |
| GB | 2486968 | B | 2/2015 |
| GB | 2542093 | A | 3/2017 |
| GB | 2561193 | B | 9/2020 |
| JP | H0474882 | A | 3/1992 |
| JP | H06152077 | A | 5/1994 |
| JP | H0910184 | A | 1/1997 |
| JP | 2000093448 | A | 4/2000 |
| JP | 2001087299 | A | 4/2001 |
| JP | 2002055074 | A | 2/2002 |
| JP | 2002224093 | A | 8/2002 |
| JP | 2005323981 | A | 11/2005 |
| JP | 2007319561 | A | 12/2007 |
| JP | 2009519751 | A | 5/2009 |
| JP | 2014033745 | A | 2/2014 |
| JP | 2014054368 | A | 3/2014 |
| KR | 101056989 | B1 | 8/2011 |
| KR | 20120003987 | A | 1/2012 |
| KR | 200485138 | Y1 | 12/2017 |
| NL | 1001019 | C2 | 2/1997 |
| NL | 1003904 | C2 | 3/1998 |
| RU | 2527155 | C2 | 8/2014 |
| TW | 201201783 | A | 1/2012 |
| WO | 1994015562 | A1 | 7/1994 |
| WO | 1997010012 | A1 | 3/1997 |
| WO | 1999033037 | A1 | 7/1999 |
| WO | 1999036017 | A1 | 7/1999 |
| WO | 2000079497 | A1 | 12/2000 |
| WO | 2001013830 | A1 | 3/2001 |
| WO | 2001050996 | A1 | 7/2001 |
| WO | 2002052302 | A2 | 7/2002 |
| WO | 2002099765 | A1 | 12/2002 |
| WO | 2005038693 | A1 | 4/2005 |
| WO | 2005082271 | A2 | 9/2005 |
| WO | 2006008866 | A1 | 1/2006 |
| WO | 2006094513 | A2 | 9/2006 |
| WO | 2007000168 | A1 | 1/2007 |
| WO | 2007059774 | A2 | 5/2007 |
| WO | 2007070266 | A1 | 6/2007 |
| WO | 2007098762 | A1 | 9/2007 |
| WO | 2007128038 | A1 | 11/2007 |
| WO | 2007133555 | A2 | 11/2007 |
| WO | 2008057884 | A2 | 5/2008 |
| WO | 2009006900 | A1 | 1/2009 |
| WO | 2009052496 | A1 | 4/2009 |
| WO | 2009107011 | A1 | 9/2009 |
| WO | 2009112912 | A2 | 9/2009 |
| WO | 2011003421 | A1 | 1/2011 |
| WO | 2011004165 | A1 | 1/2011 |
| WO | 2011061540 | A1 | 5/2011 |
| WO | 2011105701 | A2 | 9/2011 |
| WO | 2011123018 | A1 | 10/2011 |
| WO | 2011139499 | A1 | 11/2011 |
| WO | 2011161254 | A2 | 12/2011 |
| WO | 2012068386 | A1 | 5/2012 |
| WO | 2012076022 | A2 | 6/2012 |
| WO | 2012084987 | A2 | 6/2012 |
| WO | 2013013197 | A1 | 1/2013 |
| WO | 2013095231 | A1 | 6/2013 |
| WO | 2014004207 | A1 | 1/2014 |
| WO | 2014086369 | A1 | 6/2014 |
| WO | 2015007284 | A1 | 1/2015 |
| WO | 2015014774 | A1 | 2/2015 |
| WO | 2015084462 | A1 | 6/2015 |
| WO | 2015094064 | A1 | 6/2015 |
| WO | 2015187366 | A1 | 12/2015 |
| WO | 2016132738 | A1 | 8/2016 |
| WO | 2016162038 | A1 | 10/2016 |
| WO | 2016166731 | A1 | 10/2016 |
| WO | 2016192738 | A1 | 12/2016 |
| WO | 2017023794 | A1 | 2/2017 |
| WO | 2017062042 | A1 | 4/2017 |
| WO | 2017067558 | A1 | 4/2017 |
| WO | 2017067560 | A1 | 4/2017 |
| WO | 2017074505 | A1 | 5/2017 |
| WO | 2017088153 | A1 | 6/2017 |
| WO | 2017108109 | A1 | 6/2017 |
| WO | 2017136696 | A1 | 8/2017 |
| WO | 2017190752 | A1 | 11/2017 |
| WO | 2018028756 | A1 | 2/2018 |
| WO | 2019094635 | A1 | 5/2019 |
| WO | 2019120432 | A1 | 6/2019 |
| WO | 2019161859 | A1 | 8/2019 |
| WO | 2019161860 | A1 | 8/2019 |
| WO | 2019161863 | A1 | 8/2019 |
| WO | 2019174693 | A1 | 9/2019 |
| WO | 2019174695 | A1 | 9/2019 |
| WO | 2019213623 | A1 | 11/2019 |
| WO | 2020035121 | A1 | 2/2020 |

* cited by examiner

LIQUID SENSING IN OSTOMY APPLIANCE

The present disclosure relates to liquid sensing in an ostomy appliance. In particular, the present disclosure relates to a monitor device of an ostomy system configured to sense the presence of liquid and to differentiate the nature of the liquid based on electrical readings.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
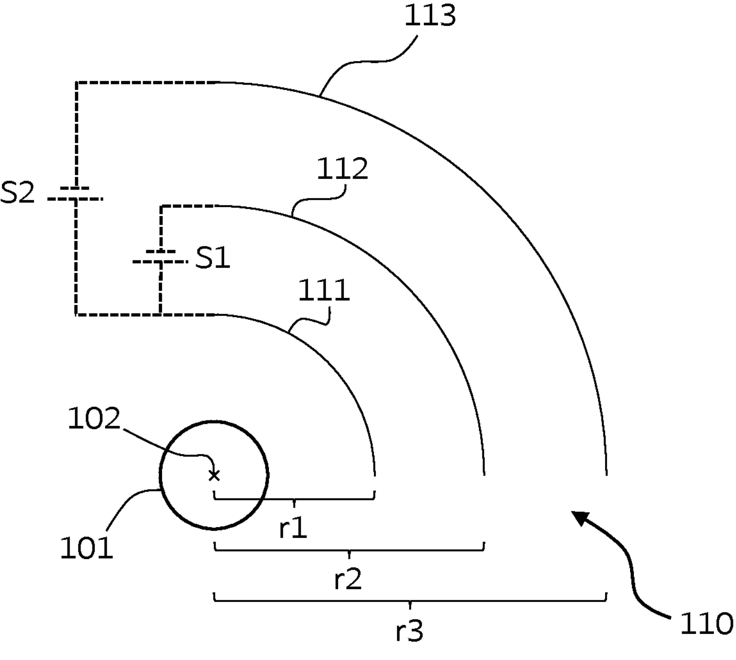
FIG. 1 illustrates an exemplary layout of electrodes of a sensor assembly according to an embodiment of the invention.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g., "stomal", "ostomies" etc. Also, the solid and liquid wastes emanating from the stoma may be referred to as both stomal "output," "waste(s)," "liquids," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do not provide the effect.

The present disclosure provides an ostomy system, a method for determining an operating state of an ostomy appliance of an ostomy system, and a monitor device of an ostomy system.

In a first aspect of the invention, an ostomy system is disclosed. The ostomy system comprises a monitor device and an ostomy appliance, the ostomy appliance comprising a sensor assembly. The sensor assembly comprises a stomal opening with a centre point. The sensor assembly comprises three or more electrodes including a first electrode arranged at a first radial distance from the centre point, a second electrode arranged at a second radial distance from the centre point, and a third electrode arranged at a third radial distance from the centre point. The second radial distance is greater than the first radial distance is greater than the first radial distance and the third radial distance is greater than the second radial distance. The first electrode and the second electrode form a primary sensor, and the first electrode and the third electrode form a secondary sensor. The monitor device comprises a processor, a memory connected to the processor, a first interface connected to the processor, the first interface being configured for connecting the monitor device to the sensor assembly. The monitor device is configured to determine a first value of an electrical quantity of, such as associated with, the primary sensor, to determine a second value of the electrical quantity of, such as associated with, the secondary sensor, and to determine an operating state of the ostomy appliance based on at least the absolute difference between the first value and the second value.

In embodiments, the sensor assembly is provided in a base plate of the ostomy appliance. In embodiments, the sensor assembly is provided in a sensor patch of the ostomy appliance, the sensor patch being configured for attachment to an adhesive proximal surface of a base plate. In embodiments, the stomal opening and the centre point of the sensor assembly is aligned with a stomal opening and centre point of a base plate or sensor patch of the ostomy appliance.

The present disclosure relates to an ostomy system and devices thereof, such as an ostomy appliance, a base plate for an ostomy appliance, a sensor patch for application to a base plate, a monitor device, and optionally one or more accessory devices. Further, methods related to the ostomy system and devices thereof are disclosed. An accessory device (also referred to as an external device) can be a mobile phone or other handheld device, such as a smart device including a smartphone or a smartwatch. In embodiments, an accessory device is a personal electronic device, e.g., a wearable, such as a watch or other wrist-worn electronic device. An accessory device can be a docking station. In embodiments, the docking station is configured to electrically and/or mechanically couple the monitor device to the docking station. In embodiments, the docking station is configured for charging a battery of the monitor device and/or configured for transferring data between the monitor device and the docking station. The ostomy system can comprise a server device. In embodiments, the server device is operated and/or controlled by the ostomy appliance manufacturer and/or a service centre.

The present disclosure provides an ostomy system and devices thereof, such as an ostomy appliance, a base plate for an ostomy appliance, a sensor patch for application to a base plate, a monitor device, and optionally one or more accessory devices which either alone or together facilitate reliable determination of the nature, severity, and rapidness of moisture propagation in the adhesive material provided for attaching the base plate and/or sensor patch to the skin surface of a user. Depending on the nature of the pattern of moisture propagation in the adhesive, the ostomy system and devices thereof enable providing information to the user about the type of failure, such as adhesive failure patterns, and in turn enable providing an indication to the user of the severity and thus the remaining time frame for replacing the ostomy appliance without experiencing severe leakage and/or skin damage.

In embodiments, the ostomy appliance includes a base plate, such as a monolithic, one-piece base plate, e.g., integrated with a sensor assembly part, or a separate sensor assembly part, such as a sensor assembly part to be subsequently applied to a base plate. In embodiments, the sensor assembly part is a sensor patch for application to the base plate, such as the proximal surface of the base plate. Thereby, an arbitrary base plate, such as a conventional base plate provided with the sensor patch, can achieve the features as described herein. Features as described with respect to sensing/monitoring capabilities of the base plate herein can be provided by a sensor assembly of a sensor patch to be applied to a base plate, e.g., by the user, and vice versa. In embodiments, the sensor patch is adapted to adhere to a base plate. In embodiments, the sensor patch comprises a first adhesive layer adapted to adhere to the skin surface of a user.

In embodiments, a method of attaching a base plate having sensing capabilities, e.g., through the provision of a sensor patch, to a user's stoma and/or skin surrounding the stoma, such as the peristomal skin area, comprises attaching the sensor patch to a base plate and attaching the base plate, i.e., together with the attached sensor patch, to the user's stoma and/or skin surrounding the stoma, such as the peristomal skin area. Alternatively, the method of attaching the base plate to the user's stoma and/or skin surrounding the stoma comprises attaching the sensor patch to the user's stoma and/or skin surrounding the stoma and attaching the base plate to the user's stoma and/or skin surrounding the stoma above the attached sensor patch, i.e., on a distal surface of the sensor patch.

In embodiments, the ostomy appliance comprises a base plate and an ostomy pouch (also referred to as an ostomy bag). The ostomy appliance can be a colostomy appliance, an ileostomy appliance, or a urostomy appliance. In embodiments, the ostomy appliance is a two-part ostomy appliance, i.e., the base plate and the ostomy pouch are releasably coupled e.g., with a mechanical and/or an adhesive coupling, e.g., to allow that a plurality of ostomy pouches can be utilized (exchanged) with one base plate. Further, a two-part ostomy appliance can facilitate correct application of the base plate to skin, e.g., to an improved user sight of the stomal region. In embodiments, the ostomy appliance is a one-part ostomy appliance, i.e., the base plate and the ostomy pouch are fixedly attached to each other. The base plate is configured for coupling to a user's stoma and/or skin surrounding the stoma, such as a peristomal skin area.

In embodiments, the ostomy system comprises a base plate or a sensor patch for application to a base plate. In embodiments, parts of the ostomy system are incorporated into a base plate or a sensor patch for application to a base plate. In embodiments, the first adhesive layer of the ostomy system is a first adhesive layer of a base plate or a sensor patch for attachment to a base plate. In embodiments, the first adhesive layer and the sensor assembly of the ostomy system are incorporated into a base plate or sensor patch to provide such with the ability to indicate a site of leakage. In embodiments, the ostomy system provides a base plate and/or a sensor patch with the ability to indicate a site of leakage from an ostomy appliance, e.g., from the base plate.

The ostomy system comprises a first adhesive layer with a proximal surface configured for attachment to the skin surface of a user and a distal surface. In embodiments, the first adhesive layer of the ostomy system is provided as part of a base plate or a sensor patch. In embodiments, the base plate and/or the sensor patch comprises the first adhesive layer and the sensor assembly of the ostomy system according to the first aspect of the invention. The first adhesive layer comprises a stomal opening, such as a first adhesive stomal opening, with a centre point, or is at least prepared for forming a stomal opening with a centre point.

During use, the first adhesive layer adheres to the user's skin (peristomal area) and/or to additional seals, such as sealing paste, sealing tape and/or sealing ring. Thus, in embodiments, the first adhesive layer is configured for attachment to the skin surface of a user, e.g., for attachment of a base plate and/or the sensor patch to the skin surface of a user. A first adhesive layer, e.g., when embodied in a base plate and/or a sensor patch, according to the present disclosure enables detection of presence of liquid or output on the proximal surface of the first adhesive layer (in the interface between a skin surface of the user, such as the peristomal skin area, and the proximal surface of the first adhesive layer).

The ostomy appliance comprises a sensor assembly. The sensor assembly has a stomal opening with a centre point, such as a stomal opening and centre point aligned with a stomal opening and centre point of a base plate and/or sensor patch incorporating the sensor assembly. In embodiments, the sensor assembly is attached to the distal surface of the first adhesive layer. In embodiments, the sensor assembly is attached to the proximal surface of the first adhesive layer. In embodiments, the sensor assembly is attachable to the distal surface or the proximal surface of the first adhesive layer. In embodiments, the sensor assembly is embedded in the first adhesive layer, i.e., the sensor assembly is covered by an adhesive layer, such as the first adhesive layer, on each (proximal and distal) side. The sensor assembly comprises at least two sensors; a primary sensor and a secondary sensor. In embodiments, the sensor assembly comprises two, three, four, five, or six sensors. In embodiments, the sensor assembly comprises more than six sensors. The sensors are arranged to facilitate detection of liquid on the proximal surface of the first adhesive layer, e.g., on the proximal surface of a base plate and/or a sensor patch incorporating parts of the ostomy system. Detection of liquid can be indicative of output present in the interface between the first adhesive layer and the skin surface, which eventually can cause leakage from the first adhesive layer, i.e., output escaping the base plate and causing distress to the user. Thus, it is desired to provide a warning before such leakage. By liquid is meant in particular all types of output emanating from a stoma, varying from highly viscous output to solid output. Further, in embodiments, by liquid is meant moisture, such as moisture absorbed by the first adhesive layer. Thus, in the following, a reference to liquid is meant at least a reference to all types of output. In the following, whenever referring to an interface is meant the interface between the first adhesive layer and the (peristomal) skin surface, unless otherwise specified.

The sensor assembly comprises three or more electrodes including a first electrode, a second electrode and a third electrode. In embodiments, the electrodes extend in an appliance plane of the sensor assembly and/or the base plate or sensor patch incorporating the sensor assembly.

The electrodes are electrically conductive and can comprise one or more of metallic (e.g., silver, copper, gold, titanium, aluminium, stainless steel or other), ceramic (e.g., ITO or other), polymeric (e.g., PEDOT, PANI, PPy or other), and carbonaceous (e.g., carbon black, carbon nanotube, carbon fiber, graphene, graphite, or other) materials. In embodiments, the electrodes can be wire electrodes or one-dimensional electrodes resembling a string or wire. In embodiments, the electrodes can have a width and/or thickness being considerably smaller than their length. In embodiments, the width and/or thickness of the electrodes can be up to 50 times smaller than the length of the electrodes. In embodiments, the electrodes can be less than 3 mm wide, and more than 100 mm long. In embodiments, the electrodes are printed on a support layer, whereby the electrodes comprise, such as consist of, conductive traces of a conductive ink, e.g., silver ink or carbon ink suitable for printing on a surface. Thus, in embodiments the electrodes comprise, such as consist of, a (hardened/cured) conductive ink. In embodiments, conductive ink is created by infusing graphite, silver, or other conductive materials, into ink. In embodiments, the support layer is stretchable, flexible and/or elastic. In embodiments, the support layer is flexible and elastic. In an embodiment, the support layer is made of a polymeric material. In embodiments, the support layer is made of polyurethane (PU), e.g., thermoplastic polyurethane (TPU). In alternative embodiments, the support layer material can be made of or comprise one or more of PTFE, PVDF, polyester (e.g., PET), a thermoplastic elastomer (TPE), polyamide, polyimide, Ethylene-vinyl acetate (EVA), polyurea, and/or silicones. Exemplary thermoplastic elastomers (TPEs) of the support layer include styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A). In embodiments, the support layer has a thickness of less than 0.1 mm, such as less than 50 μm.

In embodiments, the sensor assembly, the base plate, and/or the sensor patch comprises a monitor interface. In embodiments, the monitor interface is configured for electrically and/or mechanically connecting the ostomy appliance (base plate and/or sensor patch), in particular electrodes of the sensor assembly, to the monitor device. In embodiments, the monitor interface is configured for wirelessly connecting the ostomy appliance (base plate and/or sensor patch) to the monitor device. Thus, the monitor interface of the sensor assembly, base plate, and/or the sensor patch can be configured to electrically and/or mechanically couple the electrodes, and thus the sensors formed therefrom, and the monitor device.

In embodiments, the monitor interface of the sensor assembly, base plate, and/or the sensor patch comprises, e.g., as part of a first connector of the monitor interface, a coupling part for forming a mechanical connection, such as a releasable coupling between the monitor device and sensor assembly, base plate, and/or the sensor patch. In embodiments, the coupling part is configured to engage with a coupling part of the monitor device for releasably coupling the monitor device to the sensor assembly, base plate, and/or the sensor patch.

In embodiments, the sensor assembly is arranged on a distal side of the first adhesive layer. In embodiments, the sensor assembly is arranged at least partially in contact with a distal surface of the first adhesive layer, such that the sensor assembly may determine electrical properties of the first adhesive layer. In embodiments, the first adhesive layer is provided with a plurality of sensor point openings, such as at least 10, or at least 20, sensor point openings. In embodiments, the plurality of sensor point openings are aligned with at least parts of the three or more electrodes of the sensor assembly. In embodiments, the sensor point openings provide a passage from the proximal surface of the first adhesive layer to the distal surface of the first adhesive layer, such that liquid, such as stomal output and/or sweat, may form a bridge in the interface between the skin and the proximal surface between neighbouring electrodes, such that current may pass through the bridge of liquid and cause an electrical signal, such as a short-circuit.

The first electrode is arranged at a first radial distance r1 from the centre point, the second electrode is arranged at a second radial distance r2 from the centre point, and the third electrode is arranged at a third radial distance r3 from the centre point. The second radial distance r2 is greater than the first radial distance r1, such that r2>r1, and the third radial distance r3 is greater than the second radial distance r2, such that r3>r2, and such that r3>r2>r1. Where more than three electrodes are provided, the same relationship may apply to such further electrodes, such that the electrodes are provided at increasing (e.g., discrete) radial distances.

In embodiments, the radial distances from the centre point are fixed/constant about the centre point, such that the mutual radial distances between each of the electrodes are likewise fixed/constant. In embodiments, the radial distances vary, such as where the electrodes are provided in a wavy pattern, but the average radial distance may be constant. Thus, in embodiments, by the radial distance is meant the average radial distance, such as to account for minor wavy patterns, such as wave patterns providing a certain stretchability to the electrodes.

In embodiments, the three or more electrodes are arranged concentrically about the centre point. In embodiments, the three or more electrodes are arranged concentrically about the centre point in an angle space of at least 180 degrees, or at least 270 degrees. Thereby, a sensing coverage of at least 180 degrees or at least 270 degrees about the centre point, and as such the stoma, is provided. By concentrically is meant that the radial distance is fixed (or average thereof, as explained above) relative to the centre point for each of the three or more electrodes, and consequentially that the mutual distance (or average thereof) between neighbouring electrodes is fixed. Thereby, as will be explained further below, the monitor device may be configured to determine a speed of propagation by having such mutual radial distance stored in a memory.

The first electrode and the second electrode form a primary sensor. The first electrode and the third electrode form a secondary sensor. By forming a sensor is meant that the monitor device is configured to apply a voltage across the two electrodes forming the respective sensor. Thus, a potential difference/voltage can be applied across the sensor, i.e., across the first electrode and the second electrode to form the primary sensor and across the first electrode and the third electrode to form the secondary sensor, by means of a monitor device or a power source. In other words, in embodiments, the monitor device is configured to form a primary sensor by applying a voltage across the first electrode and the second electrode, and to form a secondary sensor by applying a voltage across the first electrode and the third electrode. Thus, in an embodiment, to determine a first value and a second value comprises applying a voltage across the primary sensor and the secondary sensor and monitoring the associated current, respectively.

By monitoring an electrical quantity across/between the two electrodes of the sensor, changes in such electrical quantity can be attributed to changing conditions of the surroundings, such as increasing or decreasing moisture content in the first adhesive layer and/or presence of liquid forming a liquid path between such two electrodes, and hence a short-circuit, between the two electrodes. Thereby is realized a sensor configured to detect/arranged to facilitate detection of liquid on the proximal surface of the first adhesive layer and hence, by means of the monitor device, provide a warning to the user that a leakage is imminent.

According to embodiments of the ostomy system disclosed herein, the primary sensor covers a region closer to the stomal opening (namely because the radial distances of the first and second electrodes forming the primary sensor are less than the radial distance of the third electrode; (r1<r2)<r3), whereas the secondary sensor covers a larger area including the region more distant (greater radial distance) from the stomal opening. In other words, the secondary sensor covers part of the region covered by the primary sensor and a region more distant from the stomal opening (in particular the region between the second electrode and the third electrode). In other words, an overlap between the primary sensor and the secondary sensor exists, namely because the first electrode forms part of both the primary sensor and the secondary sensor. In the following, the effects of this build/design are discussed in greater detail.

In embodiments, the monitor device comprises a housing, a processor, a memory connected to the processor, and a first interface connected to the processor, the first interface being configured for connecting the monitor device to the sensor assembly. In embodiments, the first interface is configured for obtaining ostomy data from the sensor assembly, e.g., the base plate and/or the sensor patch comprising a sensor assembly and coupled to the first interface. The ostomy data comprises primary ostomy data from a primary sensor of the sensor assembly, e.g., of the base plate and/or the sensor patch comprising a sensor assembly, and secondary ostomy data from a secondary sensor of the sensor assembly, e.g., of the base plate and/or the sensor patch comprising a sensor assembly. The first interface of the monitor device may comprise a plurality of terminals, such as two, three, four, five, six, seven or more terminals, for forming electrical connections with respective terminals and/or electrodes of the ostomy appliance, in particular the sensor assembly as discussed herein. One or more terminals of the first interface may be configured for forming electrical connections with an accessory device, e.g., with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The monitor device comprises a power unit for powering the monitor device. The power unit may comprise a battery. The power unit may comprise charging circuitry connected to the battery and terminals of the first interface for charging the battery via the first interface, e.g., the first connector. The first interface may comprise separate charging terminal(s) for charging the battery.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device is configured determine a first value of an electrical quantity of the primary sensor and to determine a second value of the electrical quantity of the secondary sensor. For example, the first value of an electrical quantity of the primary sensor is the size/magnitude of the concerned electrical quantity associated with the primary sensor (e.g., the resistance of material disposed between the first electrode and the second electrode), and the second value of the (same, to provide a meaningful analysis) electrical quantity of the secondary sensors is the size/magnitude of the electrical quantity associated with the secondary sensor (e.g., the resistance of material disposed between the first electrode and the third electrode).

By an electrical quantity is meant any of at least resistance, conductance, impedance, admittance, and capacitance. In an embodiment, the electrical quantity is selected from resistance, impedance, and capacitance. In embodiments, the electrical quantity is selected from the reciprocals/inverse of resistance, impedance, and capacitance. In embodiments, the electrical quantity is measured in an a.c. (alternating current) setup or a d.c. (direct current) setup.

Thus, by an electrical quantity is meant any descriptive quantity suitable for representing the electrical properties of the sensor and surroundings thereof (e.g., material disposed between the electrodes forming the sensor). In embodiments, the surroundings of a sensor herein, as is explained above, may be an adhesive composition capable of absorbing moisture or the vicinity thereof (e.g., the skin surface and liquids disposed thereon, such as in the interface), whereby the electrical properties thereof change, which will be noticeable from monitoring an electrical quantity. In an embodiment, the electrical quantity is indicative of an electrical property of an adhesive composition of the ostomy appliance and/or the sensor assembly. In embodiments, the adhesive composition is an adhesive of a base plate or a sensor patch of the ostomy appliance, such as a first adhesive layer as previously discussed. In embodiments, the electrical quantity is indicative of an electrical property of the (immediate) surroundings of the respective sensor, such as the adhesive composition and/or a surface of a layer of the ostomy appliance, such as the presence of liquid on a proximal (skin-facing) surface of the ostomy appliance.

In the following, when providing illustrative examples of the principles of the present invention, resistance is considered, but it is appreciated that such electrical quantity may as well be substituted by any of conductance, impedance, admittance and capacitance by choosing appropriate thresholds and equipment, without departing from the scope of the invention. Thus, for the purpose of discussing the principles, resistance is considered, and it is noted that presence of moisture and/or liquid in the surroundings of a sensor will cause the resistance across the sensor to decrease due to the increased conductance of current through such medium (adhesive or liquid path).

By a value of an electrical quantity is meant the numerical magnitude of the specific electrical quantity. In other words, in embodiments, the monitor device is configured to determine, e.g., the resistance (or any of the listed electrical quantities herein) of the primary sensor and the resistance of the secondary sensor.

The monitor device is configured to determine an operating state of the ostomy appliance based on at least the absolute difference between the first value and the second value. Thus, the monitor device is configured to calculate an absolute difference between, e.g., the resistances of each of the two sensors. In other words, the monitor device can determine the difference in, e.g., resistance between the primary sensor and the secondary sensor. By using the absolute difference, the choice of electrical quantity is reduced, as it is noted that using the conductance (the reciprocal of resistance) might cause a negative difference. However, for the purpose of determining an operating state, only the size, and thus the absolute, of the difference is considered according to the present embodiment. In alternative embodiments, the monitor device is configured to determine an operating state of the ostomy appliance based on at least the difference between the first value and the second value.

In embodiments, the operating state is indicative of a degree of radial erosion of the base plate, such as of the first adhesive layer, and/or the presence of (e.g., propagating) liquid in the interface between the ostomy appliance (such as a base plate or a sensor patch) and the skin surface, and as such being indicative of an acute leakage risk for the ostomy appliance. For example, an operating state may be indicative of a level of erosion of the adhesive properties of the adhesive of the base plate and/or sensor patch incorporating the sensor assembly. In embodiments, an operating state is indicative of the dynamic internal state of the ostomy appliance, related to the adhesive performance of the ostomy appliance. Adhesive performance of the ostomy appliance may be related to the condition inside the adhesive layer (e.g., which may affect by several factors such as humidity, temperature, misplacement of the ostomy appliance on the stoma, and/or malfunction of the ostomy appliance) and/or related to misplacement of the ostomy appliance on the stoma, and/or malfunction of the ostomy appliance. In embodiments, the operating state is indicative of the presence of liquid in the interface between the skin surface and the ostomy appliance, such as the position (angular and/or radial), amount and/or speed of propagation of the liquid in the interface. In embodiments, an operating state may be an indication that everything is fine, i.e., that no erosion and/or presence of liquid has been detected. Thus, in embodiments, the operating state is indicative of any condition of the ostomy appliance.

Due to the arrangement of electrodes and the corresponding formation of sensors according to embodiments of the first aspect of the invention, the operating state may, in embodiments, be determined solely based on the absolute difference between the first value and the second value of the primary and secondary sensors, respectively, as was disclosed above.

In case output starts propagating from the stoma (arranged within the stomal opening and coinciding with the centre point), it will first reach, and cause a change of, e.g., resistance, by the primary sensor. Such change is reflected by a change of the first value: in the case of monitoring resistance, the first value will decrease (e.g., short-circuit due to the presence of a liquid path between the first electrode and the second electrode) and change relative to the second value. The change of the first value due to the presence of liquid will result in an (absolute) difference between the first value and the second value since the output has not (yet) reached and formed a liquid path between the first electrode and the third electrode (i.e., across the secondary sensor). Hence, the (absolute) difference between the first value and the second value may be indicative of liquid propagating in a direction radially away from the centre point, which would most likely be stomal output. Thereby, an operating state may be determined based on the absolute difference between the first value and the second value.

Thereby is realized an ostomy system and corresponding monitor device and method for determining an operating state of an ostomy appliance by means of a simple electrode layout and a simple operation of the monitor device. In particular, since output propagates radially away from the source (the stoma), the monitor device of the ostomy system and the corresponding method is capable of differentiating stomal output from other liquids, such as sweat forming uniformly on the peristomal skin surface.

In further embodiments, an auxiliary sensor may be formed (by applying a voltage) between the second electrode and the third electrode, such as to provide a back-up for confirming the presence of liquid bridging the two sensors in the interface. Further, the presence of the auxiliary sensor may provide for determining whether liquid is propagation in a radial direction away from the stoma/centre point (e.g., most likely stomal output) or in a radial direction towards the stoma/centre point (e.g., due to external water entering the interface, e.g., due to swimming). The monitor device may be configured to determine an auxiliary value of the electrical quantity and to determine a signed difference between the auxiliary value and the first value and a signed difference between the auxiliary value the second value. Further, the monitor device may be configured to determine an operating state indicative of liquid propagating in a radial direction towards the centre point based on the signed difference between the auxiliary value and the first value. For example, where the electrical quantity is resistance, a low auxiliary value and a high first value may be indicative of liquid in the vicinity of the auxiliary sensor but not in the vicinity of the first sensor, and as such, that liquid has occurred in the outermost region of the sensor assembly; namely by the auxiliary sensor formed by the second electrode and the third electrode (being arranged at greater radial distances from the centre point than the first electrode).

Providing an ostomy system having sensing capabilities, e.g., through a base plate comprising an incorporated sensor assembly or through a sensor patch comprising a sensor assembly, provides for an optimum or improved use of an ostomy appliance of the ostomy system. In particular, it is facilitated that a base plate is not changed too late (leading to adhesive failure, leakage and/or skin damage), or at least that a user is informed that a leakage will happen, is happening, or has happened. Accordingly, the user or a health care professional is able to monitor and plan the use of the ostomy appliance. In an embodiment, the monitor device is configured to determine the operating state based on compliance of the absolute difference between the first value and the second value with a primary threshold value. In embodiments, the monitor device is configured to determine the operating state based on at least one of (i) the absolute difference between the first value and the second value and (ii) on compliance of the absolute difference between the first value and the second value with a primary threshold value.

Thereby, the first value must change a certain amount relative to the second value (i.e., the absolute difference has to be larger than the primary threshold value) before the operating state is changed, such as to be indicative of the presence of liquid, in particular output, in the interface. Thereby is provided a system providing for the operating state not changing too often, but only when a significant change (determined by the value of the primary threshold value) in the absolute difference occurs.

In an embodiment, the monitor device is configured to determine a first initial baseline of the electrical quantity of the primary sensor and a second initial baseline of the electrode quantity of the secondary sensor in response to a connection between the monitor device and the sensor assembly. Thereby, in response to the monitor device being connected to the sensor assembly, the monitor device is configured to determine a first and second initial baseline of the primary and secondary sensors, respectively. For example, the first and second initial baselines are the average first and second values, respectively, collected within a certain time-period, such as less than 5 minutes, following the connection between the monitor device and the sensor assembly. Thereby, such baselines may form basis for further data analysis, as it may be assumed, at least by the monitor device, that the first and second initial baselines are the respective initial values of the primary and secondary sensors prior to exposure to moisture, liquid, or other substances. In embodiments, the time-period for determination of the first and second initial baselines may be less than 10 minutes following the connection between the monitor device and the sensor assembly. Alternatively, the time-period may be between 5 seconds and 10 minutes, such as between 10 seconds and 5 minutes. In general, the time-period should be less than the time between application of the ostomy appliance to the skin surface and an expected onset of changes in the adhesive performance of the base plate or sensor patch incorporating the sensor assembly, such as changes due to absorption of moisture, such as sweat.

In an embodiment, the determination of the operating state is based on a deviation of the first value from the first initial baseline and/or a deviation of the second value from the second initial baseline. Thereby, the operating state may be determined based on the absolute difference and a deviation of any of the first and second values from their respective initial baselines. In embodiments, a deviation of any of the first and second values from the respective initial baselines may be a deviation by at least a secondary threshold value from the respective initial baseline. Thereby, minor fluctuations do not cause the determination of a (new) operating state, whereas larger deviations, exceeding such secondary threshold value may cause a change of operating state.

For example, where an operating state indicative of stomal output in the vicinity of the primary sensor (example provided above) was previously determined, a new operating state may be determined by further considering a deviation of any of the first and second values from their respective initial baselines. For example, in an embodiment, the determination of the operating state is based on a previous operating state and on a deviation of the second value from the second initial value. In particular, following an operating state indicative of stomal output in the vicinity of the primary sensor, the monitor device may update/determine a new operating state if the monitor device determines that the second value deviates from the second initial baseline. If the previous operating state was indicative of stomal output in the interface by the primary sensor, a change of value of the second value is likely caused by the stomal output having propagated to cause the change of the second value. In other words, the monitor device may determine a new operating state indicative of the stomal output having propagated to the third electrode (as this forms part of the secondary sensor).

Thereby is realised a monitor device and corresponding method for detecting the propagation of output in the interface by means of solely the absolute difference (as used to determine the previous operating state) and the deviation of the second value from the second initial baseline.

On the contrary, the monitor device may determine an operating state indicative of sweat/moisture forming in the interface if the absolute difference between the first and second values remains constant (such as below the primary threshold value) but both the first value and the second value deviate from their respective initial baselines. For example, the formation of sweat is likely to form uniformly about the stoma and cause erosion of the adhesive in contact with the sensor assembly, and such erosion may be detected through a uniform decrease of resistance Thereby, the monitor device and corresponding method is capable of detecting, and differentiating, stomal output from sweat by means of the same sensors (primary and secondary sensors) and without requiring modification of the adhesive layer. In particular, the monitor device and corresponding method according to the present disclosure is capable of providing selectivity towards the type of liquid (stomal output or sweat) and indication on propagation of output by means of a sensor assembly comprising merely three electrodes forming two sensors.

In embodiments, the monitor device is configured to determine the operating state based on at least one of (i) the absolute difference between the first value and the second value, (ii) on compliance of the absolute difference between the first value and the second value with a primary threshold value, (iii) a deviation of the first value from the first initial baseline and/or a deviation of the second value from the second initial baseline and (iv) a previous operating state and on a deviation of the second value from the second initial value.

In an embodiment, the determination of the operating state is based on a time difference between a deviation of the first value from the first initial baseline and a deviation of the second value from the second initial baseline. Thus, in embodiments, the monitor device is configured to record a first time stamp indicative of the time of recording the first value deviating from the first initial baseline and to record a second time stamp indicative of the time of recording the second value deviating from the second initial baseline, and to determine a time difference based on said first time stamp and second time stamp.

In embodiments, a deviation of any of the first and second values from the respective initial baselines may be a deviation by at least a secondary threshold value from the respective initial baseline. Thereby, minor fluctuations do not cause the determination of a (new) operating state, whereas larger deviations, exceeding such secondary threshold value may cause a change of operating state.

In embodiments, the radial distance between the three or more electrodes is fixed/constant and stored in a memory of the monitor device. By considering the time difference between deviations of the first and second values from their respective initial baselines, a speed of propagation may be determined based on such time difference. In particular, the speed of propagation may be determined in units of length per unit time, such as mm/min, if the radial distance between the electrodes is known. Thereby, the operating state may be indicative of a speed of propagation of output propagating in the interface between the skin surface and the ostomy appliance or be indicative of an urgency of action needed to avoid leakage onto clothes.

In embodiments, a high time difference, such as a time difference above a first time threshold, may be indicative of a slow propagation of output and/or indicative of presence of sweat rather than output, such as if the time difference is above a second time threshold greater than the first time threshold. In embodiments, a low time difference, such as a time difference lower than a third time threshold, may be indicative of a quickly propagating output in the interface.

As such, the time difference, in particular in combination with the fixed distance between the electrodes, provides further insights into the nature of the liquid as detected in the interface, as is reflected by the determined operating state.

In embodiments, the monitor device is configured to determine the operating state based on at least one of (i) the absolute difference between the first value and the second value, (ii) on compliance of the absolute difference between the first value and the second value with a primary threshold value, (iii) a deviation of the first value from the first initial baseline and/or a deviation of the second value from the second initial baseline, (iv) a previous operating state and on a deviation of the second value from the second initial value and (v) a time difference between a deviation of the first value from the first initial baseline and a deviation of the second value from the second initial baseline.

In an embodiment, the operating state is selected from a plurality of operating states including an operating state indicative of presence of stomal output in an interface between the skin surface and the ostomy appliance and an operating state indicative of presence of sweat in the interface. In embodiments, the operating state indicative of presence of sweat in the interface may be an operating state indicative of moisture absorbed in an adhesive composition of the base plate or the sensor patch of the ostomy appliance. Further, the plurality of operating states may include a default operating state indicative of neither presence of stomal output nor sweat/moisture.

For example, as previously discussed, in an embodiment, in accordance with at least the absolute difference being in non-compliance with the primary threshold value, the operating state is indicative of presence of stomal output in the interface.

Thereby, based on, in embodiments, a single parameter—the absolute difference—an operating state may indicate the reason to liquid in the interface; presence of stomal output or presence of sweat. In other words, the layout of electrodes including as few as three electrodes may be used, by appropriate configuration of the monitor device according to embodiments of the present invention, to determine operating states indicative of different sources of liquid in an interface between a skin surface and an ostomy appliance.

In embodiments, the plurality of operating states includes at least two, such as at least three, operating states. In embodiments, the plurality of operating states includes between 2 and 10 operating states, such as between 3 and 10 operating states, such as between 3 and 6 operating states. Thereby, a user is presented a limited number of operating states, such that the presented information is more comprehensible. For example, the limited number of operating states may be formed by appropriate use of threshold values, such that minor changes of the first and second values of the electrical quantity are grouped in a single operating state.

In an embodiment, the monitor device further comprises a second interface comprising a transceiver module connected to the processor and configured for connecting the monitor device to an accessory device of the ostomy system. In an embodiment, the monitor device is configured to transmit a primary signal indicative of the operating state. The second interface may be configured as an accessory interface for connecting, e.g., wirelessly connecting, the monitor device to one or more accessory devices. The second interface may comprise an antenna and a wireless transceiver, e.g., configured for wireless communication at frequencies in the range from 2.4 to 2.5 GHz. The wireless transceiver may be a Bluetooth transceiver, i.e., the wireless transceiver may be configured for wireless communication according to Bluetooth protocol, e.g., Bluetooth Low Energy, Bluetooth 4.0, Bluetooth 5. The second interface optionally comprises a loudspeaker and/or a haptic feedback element for provision of an audio signal and/or haptic feedback to the user, respectively.

Thereby, the determined operating state and/or related data may be transmitted, through the primary signal indicative of such operating state and/or related data, to an accessory device, such as a smartphone running an app configured to indicate the operating state, such as in a graphical user interface.

In a second aspect of the invention, a method, performed in a monitor device of an ostomy system, for determined an operating state of an ostomy appliance of the ostomy system is disclosed. The ostomy appliance comprises a sensor assembly having a stomal opening with a center point. The sensor assembly comprises three or more electrodes including a first electrode arranged at a first radial distance from the center point, a second electrode arranged at a second radial distance from the center point, and a third electrode arranged at a third radial distance from the center point, wherein the second radial distance is greater than the first radial distance and the third radial distance is greater than the second radial distance. The first electrode and the second electrode form a primary sensor, and the first electrode and the third electrode form a secondary sensor. The monitor device comprises a processor, a memory connected to the processor, and a first interface connected to the processor, the first interface being configured for connecting the monitor device to the sensor assembly. The method comprises the steps of determining a first value of an electrical quantity of the primary sensor, determining a second value of the electrical quantity of the secondary sensor, and determining an operating state of the ostomy appliance based on at least the absolute difference between the first value and the second value.

The method is performed in a monitor device of an ostomy system. In embodiments, the method comprises the initial step of coupling the monitor device to the sensor assembly. In embodiments, the monitor device is connected by means of a mechanical coupling to terminals of the electrodes of the sensor assembly, such as in a monitor interface of the sensor assembly. In embodiments, the method comprises the initial step of applying the ostomy appliance, such as a base plate or a sensor patch incorporating the sensor assembly, to the (peristomal) skin surface of a user.

In embodiments, the method is repeated/reiterated during use, such as for the duration of the monitor device being coupled to the sensor assembly. For example, the method may comprise repeatably determining the first and second values and determining an operating stated based on at least the absolute difference for each iteration of the method.

It is appreciated that functionalities of the monitor device and ostomy system as disclosed herein in relation to the first aspect of the invention are applicable to the method as disclosed herein in relation to the second aspect of the invention, and vice versa. Further, definitions relating to, and embodiments of, the monitor device and ostomy system are considered applicable to the method as disclosed herein. Thus, it is appreciated that disclosures of the monitor device as being configured to perform certain acts also apply to the corresponding acts in the method of operating such monitor device and vice versa.

For example, in embodiments, the step of determining the operating state may comprise determining the operating state based on at least one of (i) the absolute difference between the first value and the second value, (ii) on compliance of the absolute difference between the first value and the second value with a primary threshold value, (iii) a deviation of the first value from a first initial baseline and/or a deviation of the second value from a second initial baseline, (iv) a previous operating state and on a deviation of the second value from the second initial value and (v) a time difference between a deviation of the first value from the first initial baseline and a deviation of the second value from the second initial baseline.

In embodiments, the monitor device further comprises a second interface comprising a transceiver module connected to the processor and configured for connecting the monitor device to an accessory device of the ostomy system, and the method comprises the additional step of transmitting a primary signal indicative of the operating state to the accessory device.

Thus, in embodiments, the method comprises, in accordance with determining an operating state of the monitor device, transmitting a primary signal indicative of such operating state to an accessory device of the ostomy system. The accessory device may be a smart device, such as a smartphone, a smartwatch, a tablet, or it may be a server device. In embodiments, the primary signal is transmitted wirelessly, such as by means of the second interface as previously disclosed.

Thereby, the user may be notified of the determined operating state by means of his/her accessory device, such as in a graphical user interface of the accessory device.

In alternative embodiments, the method is performed in an accessory device connected, such as wirelessly connected, to the monitor device, such that the monitor device may relay raw data indicative of the first and second values to the accessory device, and such that the accessory device may perform the step of determining the operating state and associated steps of the method relating to the determination of the first and second base lines, time deviations, etc.

In a third aspect of the invention, a monitor device of an ostomy system comprising a sensor assembly is disclosed. The monitor device is configured to perform the steps of the method according to the second aspect of the invention. The ostomy system may be the ostomy system according to the first aspect of the invention.

DETAILED DESCRIPTION OF THE DRAWINGS

FIG. 1 illustrates an exemplary layout of electrodes 110 of a sensor assembly according to an embodiment of the invention. The sensor assembly forms part of an ostomy appliance, such as a base plate or a sensor patch, and comprises a stomal opening 101 with a center point 102. The stomal opening 101 may be defined by a support layer (not shown) of the sensor assembly support the electrodes 110. The sensor assembly comprises a first electrode 111, a second electrode 112 and a third electrode 113. The first electrode 111 is arranged at a first radial distance r1 from the center point 102, the second electrode 112 is arranged at a second radial distance r2 from the center point 102, and the third electrode 113 is arranged at a third radial distance r3 from the center point 102. The second radial distance r2 is greater than the first radial distance r1; r2>r1, and the third radial distance r3 is greater than the second radial distance r2; r3>r2, such that r1<r2<r3. In the illustrated embodiment, the electrodes span an angle space of 90 degrees about the center point 102, but in alternative embodiments, they may span angle space of at least 180 degrees, such as at least 270 degrees, such as to provide even greater sensing coverage about the stomal opening 102. The electrodes 111,112,113 may, as illustrated, be arranged concentrically about the center point 102, such that their respective radial distances r1,r2,r3 are constant about the center point 102, and such that the mutual radial distances between the electrodes are constant.

By means of a monitor device (not shown) coupled to the sensor assembly, a voltage is applied across the first electrode 111 and the second electrode 112, thus forming a primary sensor S1. The primary sensor S1 is, at least, capable of sensing changes in the environment between the first electrode 111 and the second electrode 112, such as the presence of a liquid or moisture causing a change in an electrical quantity, such as the electrical resistance, between said electrodes. Likewise, a voltage is applied across the first electrode 111 and the third electrode 113, thus forming a secondary sensor S2. The secondary sensor S2 is, at least, capable of sensing changes in the environment between the first electrode 111 and the third electrode 113, such as the presence of a liquid or moisture causing a change in an electrical quantity, such as the electrical resistance, between said electrodes.

Figure 2A:
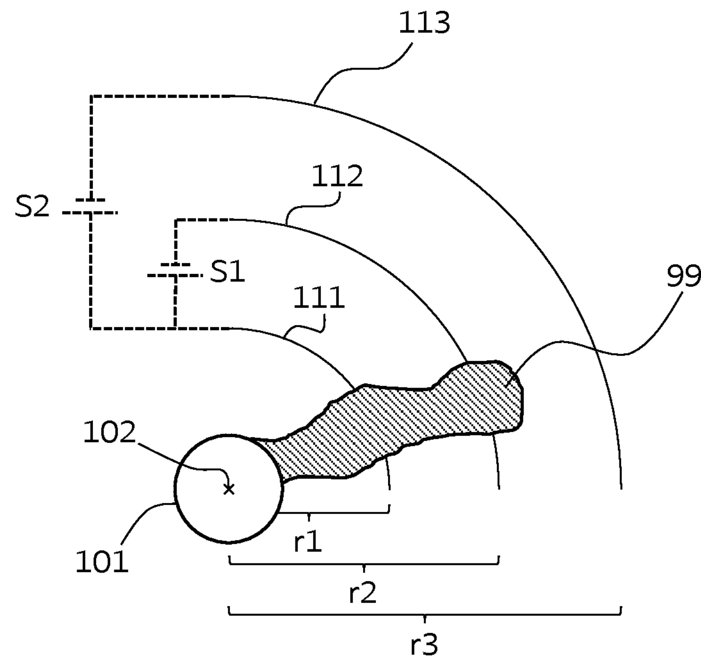
FIG. 2A illustrates an exemplary situation of a liquid 99, emanating from the stomal opening 101, causing a bridge to form between the first electrode 111 and the second electrode 112 of the sensor assembly.

FIG. 2A illustrates an exemplary situation of a liquid 99, emanating from the stomal opening 101, causing a bridge to form between the first electrode 111 and the second electrode 112 of the sensor assembly. Such bridge provides a path for the current, and thus causes the resistance between the first electrode 111 and the second electrode 112 to decrease, such as to form a short-circuit. Because the liquid does not bridge between the first electrode 111 and the third electrode 113, the resistance therebetween is essentially unaffected by the presence of the bridge between the first electrode 111 and the second electrode 112. Consequentially, the absolute difference between the resistance of the primary sensor S1 and the resistance of the secondary sensor S2 increases, such as increases above a primary threshold value (e.g., for triggering a change in operating state). Thereby, the monitor device may determine that liquid has occurred in the vicinity of the primary sensor S1, but not in the (entire) vicinity of the secondary sensor S2: namely, since the secondary sensor S2 spans the primary sensor S1 due to the arrangement of electrodes and configuration of the monitor device, a change in absolute difference between the first and second values must be due to liquids in the vicinity of the primary sensor S1 only. Further, because the presence of liquid has been determined in the vicinity of the primary sensor S1, which is composed of electrodes 111,112 radially closer to the stomal opening 101 than the electrodes of the secondary sensor S2, the monitor device may determine that the liquid stems from features in such vicinity, which is most likely the stoma. Therefore, the monitor device may determine an operating state of the ostomy appliance, the operating state according to the present example being indicative of the presence of stomal output in the interface between the skin surface and the ostomy appliance. The monitor device may be configured to provide a signal and/or a warning to the user that attention is needed, as described herein.

Figure 2B:
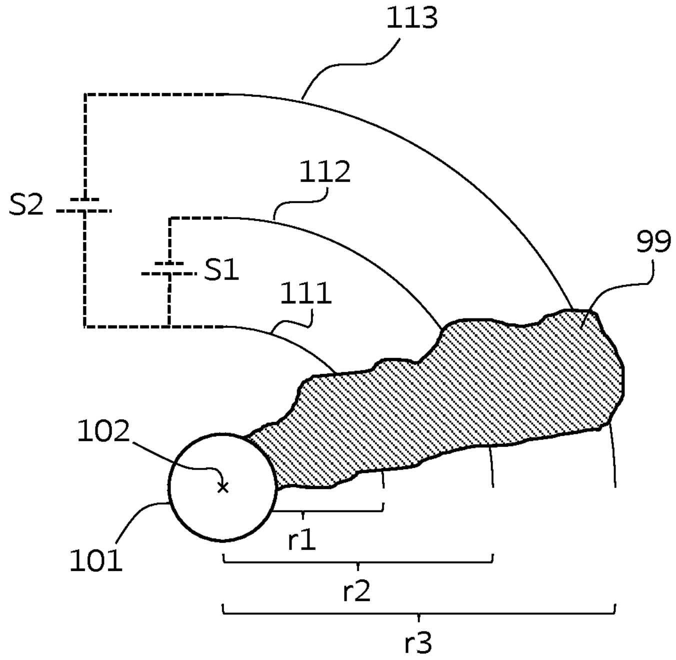
FIG. 2B illustrates an evolving case of the exemplary situation in FIG. 2A.

FIG. 2B illustrates an evolving case of the exemplary situation in FIG. 2A. Here, the liquid 99 has propagated to reach the third electrode 113 such that the liquid further causes a short-circuit of the secondary sensor S2 comprising the first electrode 111 and the third electrode 113. Now, the monitor device may determine that liquid spans from the first 111 to the third electrode 113, such that said liquid has propagated from spanning the first 111 and the second electrode 112, forming the primary sensor S1, to now having reached the third electrode 113. Thereby, the monitor device may determine, given that it was previously determined, in relation to FIG. 2A, that the liquid is indeed stomal output (originating from the stomal opening), that the output is propagating further, and as such, the monitor device may determine a new operating state indicative of such propagation. Further, based on the mutual distance between the electrodes, in particular the radial distance between the second electrode 112 and the third electrode 113, given by r3−r2 due to the concentrical layout of electrodes, the monitor device may determine a speed of propagation based on a time difference between determining the operating state indicative of presence of output and the (new) operating state indicative of the propagation of output.

Figure 3A:
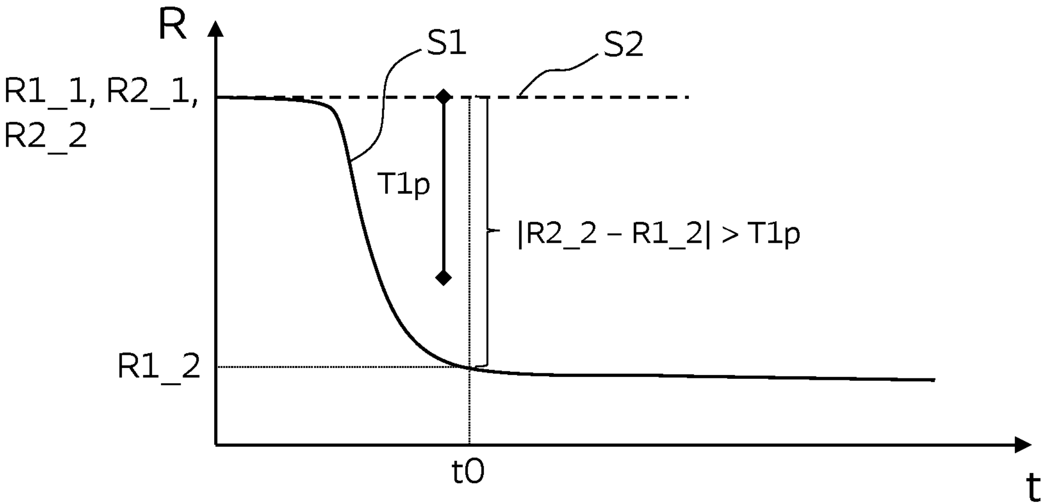
FIG. 3A illustrates a schematic graph of the electrical resistance R as a function of time t, R(t), for each of the primary sensor S1 and the secondary sensor S2 (dashed) in an exemplary case.

FIG. 3A illustrates a schematic graph of the electrical resistance R as a function of time t, R(t), for each of the primary sensor S1 and the secondary sensor S2 (dashed) in an exemplary case. The primary sensor S1 is formed by a voltage applied across the first electrode 111 and the second electrode 112, and the secondary sensor S2 is formed by a voltage applied across the first electrode 111 and the third electrode 113, as explained in relation to FIG. 1.

In the illustrated example, the resistance of the primary sensor S1 has dropped from the value R1_1 to the value R1_2 at time t0 while the resistance R2_2 of the secondary sensor S2 has remained constant at the value R2_1, such that R2_1=R2_2 at time t0. Such situation may indicate that liquid has short-circuited (decreased resistance) the primary sensor S1, whereas the secondary sensor S2 remains unaffected by such liquid (i.e., "dry"). According to embodiments of the invention, the monitor device is configured to continuously (here, considered at time t0) determine a first value (here, R1_2) of an electrical quantity (here, resistance) of the primary sensor S1 and a second value (here, R2_2) of the (same) electrical quantity (hence, resistance) of the secondary sensor S2. Based on such determinations of the resistances of each of the two sensors S1,S2, the monitor device can determine the absolute difference in resistance |R2_2−R1_2| between the two sensors. In accordance with such absolute difference |R2_2−R1_2| being above a primary first threshold T1*p* (in FIG. 3A indicated for illustrative purposes as a range on the y-axis R), the monitor device is configured to determine that liquid is present in the interface between the skin surface and the ostomy appliance—and in particular in the vicinity of the primary sensor S1.

Namely, the drop in resistance of the primary sensor S1 occurring before a similar drop in resistance of the secondary sensor S2 is indicative of liquid not having reached the third electrode 113 of the secondary sensor S2 at time t0, and as such, the liquid must originate from the stomal opening, which indicates that the liquid is indeed stomal output. Thereby, based on the difference of resistance between the two sensors S1,S2 alone, the monitor device may determine the presence of stomal output in the interface. As was explained in relation to FIG. 1, this analysis applies to the situation where the primary sensor S1 is formed by a first electrode and a second electrode, the first electrode being arranged at a first radial distance from the stomal opening (e.g., center point thereof) and the second electrode being arranged at a second radial distance from the stomal opening (e.g., center point thereof), the second radial distance being greater than the first radial distance, and where the secondary sensor S2 is formed by the first electrode and a third electrode, the third electrode being arranged at a third radial distance from the stomal opening (e.g., center point thereof), the third radial distance being greater than the second radial distance.

Figure 3B:
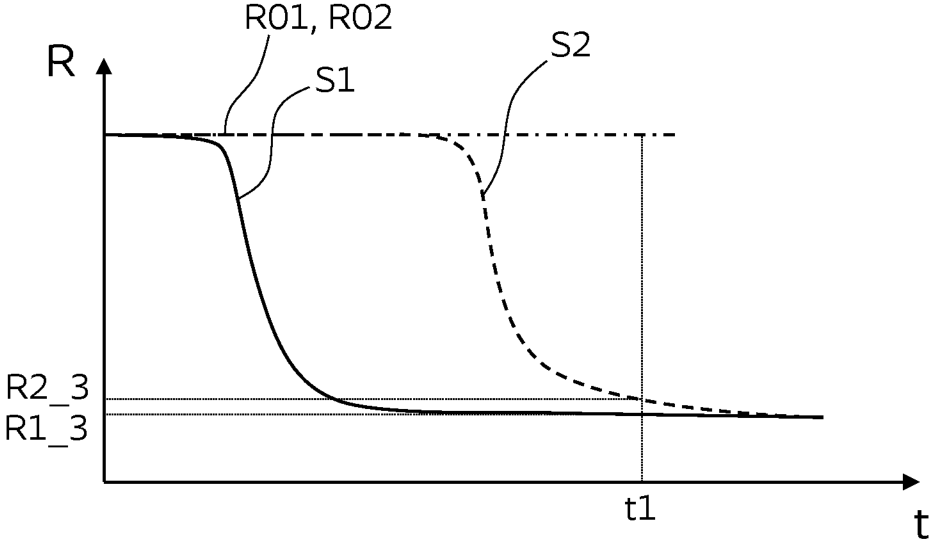
FIG. 3B illustrates a schematic graph of the electrical resistance R as a function of time t, R(t), for each of the primary sensor S1 and the secondary sensor S2 (dashed) in an evolved situation of the case in FIG. 3A.

FIG. 3B illustrates a schematic graph of the electrical resistance R as a function of time t, R(t), for each of the primary sensor S1 and the secondary sensor S2 (dashed) in an evolved situation of the case in FIG. 3A. Here, at time t1, the secondary sensor S2 has experienced a similar drop in resistance as the primary sensor S1 at time t0. Further, indicated is the first initial baseline R01 and the second initial baseline R02 (dashed-dotted, coinciding) representing the initial value of resistance of each of the two sensors S1,S2, such as the initial average values of the respective resistances as measured upon connection between the monitor device and the sensor assembly, such as within a first time period upon such connection. The first R01 and second initial baselines R01 represent the resistances of the respective sensors S1,S2 in a dry/clean situation.

At time t1, each of the first value R1_3 and the second value R2_3 are below the respective first initial baseline R01 and the second initial baseline R02: R1_3<R01 and R2_3<R02. This indicates that liquid has caused the resistance of the secondary sensor S2 to decrease similar to the resistance of the primary sensor S1. Since the previously determined operating state was indicative of the presence of output in the interface (discussed in relation to FIG. 3A), the monitor device may determine a new operating state, taking into account the previous operating state and the situation of R1_3<R01 and R2_3<R02. Therefrom, the new operating state may be determined to be indicative of a propagation of the output in the interface. In embodiments, the time difference between the determination of the previous operating state indicative of presence of liquid in the vicinity of the primary sensor S1 and the determination of the current operating state indicative of the propagation of the liquid may be used to determine the speed of propagation, and as such an urgency of the current operating state. For example, where the speed of propagation is high, such as above a threshold, the urgency may be considered high due to the risk of imminent leakage of output onto the user's clothes, whereas a low speed of propagation may give the user more time to take remedying actions.

Figure 3C:
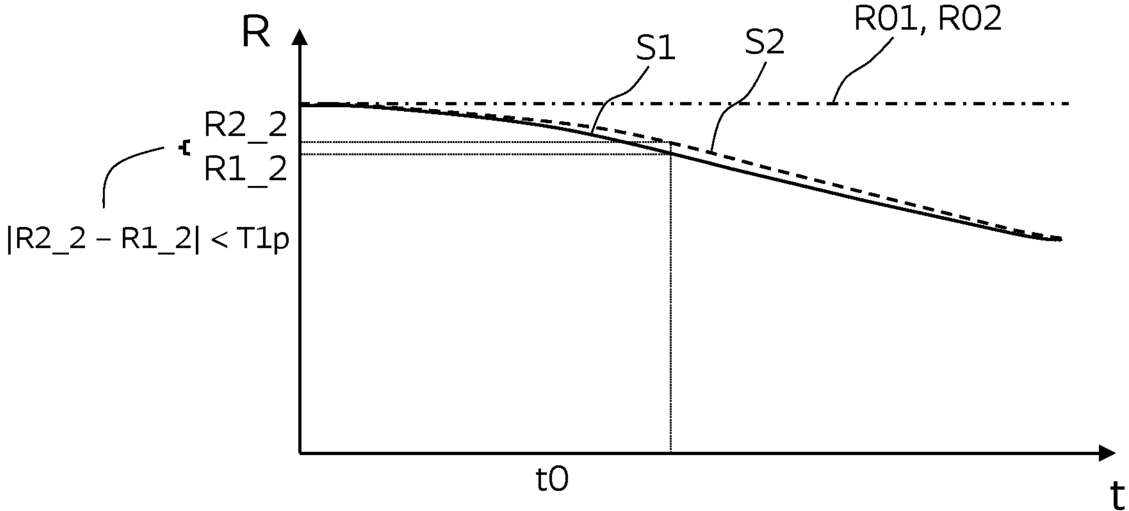
FIG. 3C illustrates a schematic graph of the electrical resistance R as a function of time t, R(t), for each of the primary sensor S1 and the secondary sensor S2 (dashed) in an exemplary case.

FIG. 3C illustrates a schematic graph of the electrical resistance R as a function of time t, R(t), for each of the primary sensor S1 and the secondary sensor S2 (dashed) in an exemplary case. In this case, at time t0, the absolute difference between the first resistance R1_2 and the second resistance R2_2, |R2_2−R1_2|, is less than a first primary threshold value T1*p*. Further, the first resistance R1_2 is below the first initial baseline R01 (dashed-dotted) of the primary sensor S1, and the second resistance R2_2 is below the second initial baseline R02 (dashed-dotted) of the secondary sensor S2. Based on at least the absolute difference, the monitor device may determine that the measurements are not indicative of stomal output in the interface. Further, based on the deviations of the first R1_2 and second resistances R2_2 from the respective initial baselines R01, R02, the monitor device may determine that the measurements are indicative of moisture, such as sweat, absorbed by the adhesive layer of the ostomy appliance in contact with the primary sensor S1 and the secondary sensor S2. Thus, the operating state may be determined to be an operating state indicative of the presence of moisture and/or sweat having formed uniformly in a radial direction from the stoma, thus giving rise to the substantially identical decrease of resistance by each of the two sensors S1,S2.

Figure 4:
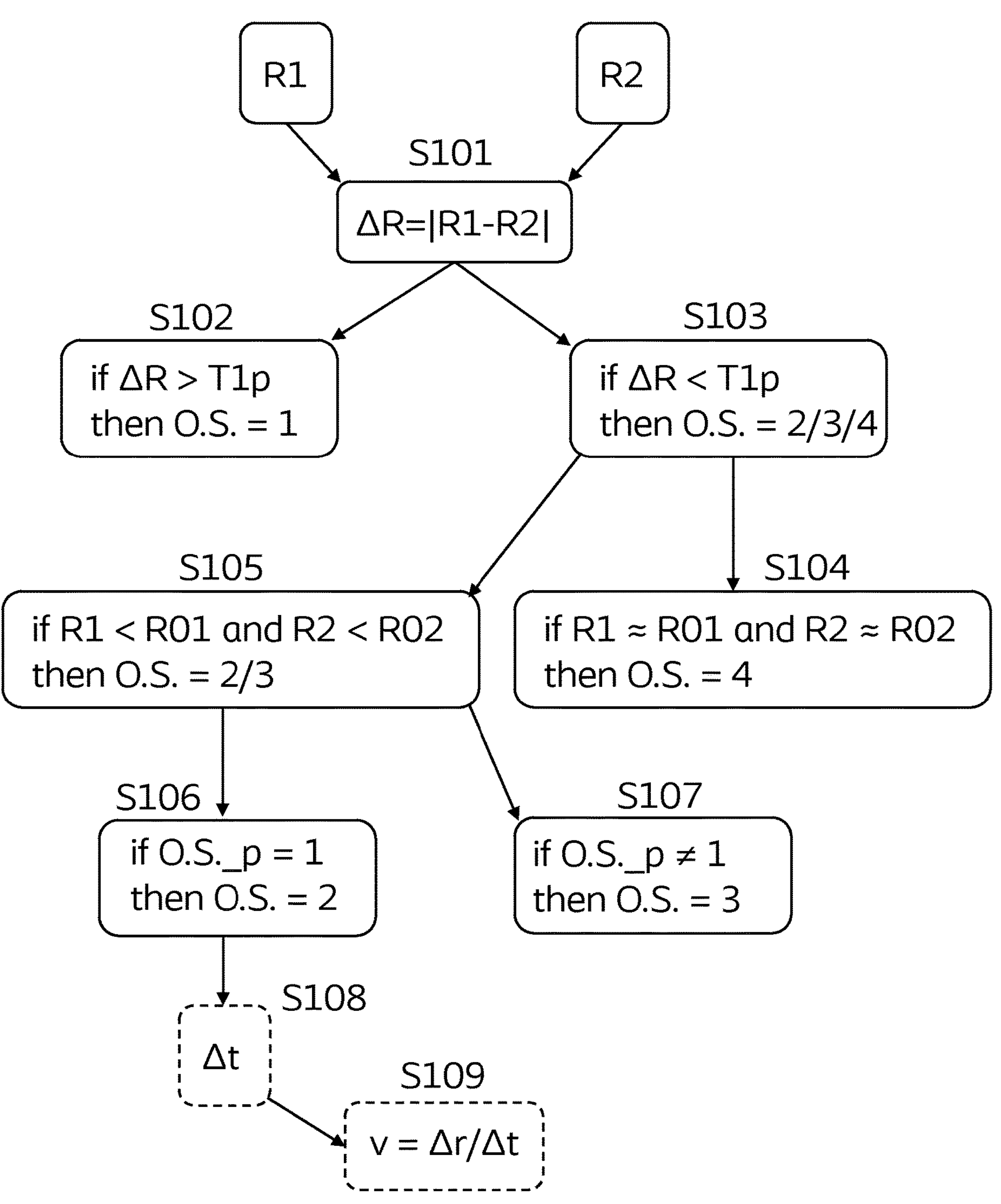
FIG. 4 illustrates a flow diagram of an exemplary method of determining an operating state of an ostomy appliance of an ostomy system as performed in a monitor device of the ostomy system.

FIG. 4 illustrates a flow diagram of an exemplary method of determining an operating state of an ostomy appliance of an ostomy system as performed in a monitor device of the ostomy system. For illustrative purposes, the electrical quantity considered in the present method is resistance, but it is appreciated that other electrical quantities may be used upon selecting appropriate threshold values. Further, it should be noted that further parameters or values may be used in the determination of the various operating states, but the flow diagram intends to illustrate how such various operating states may be determined based on solely two sensors comprising three electrodes (see e.g., FIGS. 3A-3C) and an application of voltage forming a primary sensor and a secondary sensor as previously disclosed. For illustrative purposes, the monitor device is configured to determine four different operating states O.S. using the references 1, 2, 3, and 4. In other embodiments, the monitor device may be configured to determine fewer operating states, such as at least two operating states. In embodiments, the monitor device may be configured to determine more than four operating states. The four operating states referred to herein are the first operating state 1 indicative of presence of stomal output in the interface by the primary sensor, the second operating state 2 indicative of a propagating stomal output in the interface, the third operating state 3 indicative of sweat in the interface/absorbed in an adhesive layer of the ostomy appliance, and the fourth operating state 4 indicative of no change from initial application of the ostomy appliance. Thus, the fourth operating state 4 may be considered a default operating state where no change has been detected since initial application.

The monitor device is initially configured to determine the resistance R1 (the first value as referred to previously) of the primary sensor and the resistance R2 (the second value as referred to previously) of the secondary sensor.

In step S101, the absolute difference ΔR=|R1−R2| between the two resistances is determined.

In step S102, if ΔR is greater than a primary threshold value T1*p*, the monitor device may determine that the operating state O.S. is the first operating state, O.S.=1 (indicative of presence of stomal output by the primary sensor).

In step S103, if ΔR is less than the primary threshold value T1*p*, the monitor device may determine that the operating state O.S. is either the second, the third, or the fourth operating state; O.S.=2/3/4.

In step S104, if the first resistance R1 is substantially unchanged from its first initial baseline R01 and if the second resistance R2 is substantially unchanged from its second initial baseline R02, the monitor device may determine that the operating state O.S. is the fourth operating state; O.S.=4 (indicative of no change from initial application of the ostomy appliance.

In step S105, if the first resistance R1 is less than its first initial baseline R01 (such as if less than a threshold value indicative of a drop below the first initial baseline R01) and if the second resistance R2 is less than its second initial baseline R02 (such as if less than a threshold value indicative of a drop below the second initial baseline R02), the monitor device may determine that the operating state O.S. is either the second or the third operating state; O.S.=2/3.

In step 106, if the previous operating state O.S._p (such as determined in a previous iteration of the flow diagram) was determined not to be the first operating state; O.S._p≠1, the monitor device may determine that the operating state is the third operating state; O.S.=3 (indicative of sweat in the interface).

In step S107, if the previous operating state O.S._p (such as determined in a previous iteration of the flow diagram) was determined to be the first operating state; O.S._p=1, the monitor device may determine that the operating state is the second operating state; O.S.=2 (indicative of a propagation of stomal output, i.e., the presence of stomal output as determined according to the previous operating state O.S._p has propagated to the secondary sensor).

In step S108 (dashed; optional), the monitor device may determine the time difference Δt between the monitor device determining that the operating state is the first operating state, O.S.=1, and the monitor device determining that the operating state is the second operating state, O.S.=2. Thus, such time difference Δt is indicative of the time between output having been determined to be present by the primary sensor and output having been determined to be present by the secondary sensor.

In step S109 (dashed; optional), the monitor device may determine the speed of propagation v, based on the time difference $\Delta t$ as determined in step S108 and on a radial distance $\Delta r$ between the second electrode and the third electrode: $v=\Delta r/\Delta t$. The distance $\Delta r$ may be stored in a memory of the monitor device. The speed of propagation v may be indicative of an urgency of the second operating state O.S.=2. For example, the second operating state may comprise a plurality of secondary second operating states, such that, based on the speed of propagation, a certain operating state of the secondary second operating state indicative of the urgency may be selected. For example, a set of threshold values associated with the speed of propagation may determine the urgency, and as such the secondary second operating state.

In FIG. 4, the monitor device may be configured to transmit a primary signal indicative of any of the operating states 1/2/3/4, such as to transmit a primary signal to an accessory device comprising a visual interface configured to notify the user of the determined operating state.

Although particular features have been shown and described, it will be understood that they are not intended to limit the claimed invention, and it will be made obvious to those skilled in the art that various changes and modifications may be made without departing from the spirit and scope of the claimed invention. For example, it is envisioned that the sensor assembly and the electrodes thereof may be incorporated and/or provided in a variety of different embodiments without departing from the scope of the invention.

The specification and drawings are, accordingly, to be regarded in an illustrative rather than restrictive sense. The claimed invention is intended to cover all alternatives, modifications, and equivalents.

The invention claimed is:

1. An ostomy system, comprising:

an ostomy appliance comprising a sensor assembly, wherein the sensor assembly comprises a stomal opening with a center point and three or more electrodes including a first electrode arranged at a first radial distance from the center point, a second electrode arranged at a second radial distance from the center point, and a third electrode arranged at a third radial distance from the center point, wherein the second radial distance is greater than the first radial distance and the third radial distance is greater than the second radial distance, wherein the first electrode and the second electrode form a primary sensor and wherein the first electrode and the third electrode form a secondary sensor; and a monitor device comprising a processor, a memory connected to the processor, and a first interface connected to the processor and configured for connecting the monitor device to the sensor assembly, and wherein the monitor device is configured to:

determine a first value of an electrical quantity for the primary sensor, wherein the electrical quantity is indicative of an electrical property of an adhesive composition of the ostomy appliance and/or the sensor assembly;

determine a second value of the electrical quantity for the secondary sensor; and determine an operating state of the ostomy appliance based on at least an absolute difference between the first value and the second value.

2. The ostomy system according to claim 1, wherein the monitor device is configured to determine the operating state based on compliance of the absolute difference between the first value and the second value with a primary threshold value.

3. The ostomy system according claim 1, wherein the monitor device is configured to determine a first initial baseline of the electrical quantity for the primary sensor and a second initial baseline of the electrical quantity for the secondary sensor in response to a connection between the monitor device and the sensor assembly.

4. The ostomy system according to claim 3, wherein the determination of the operating state is based on a deviation of the first value from the first initial baseline and/or a deviation of the second value from the second initial baseline.

5. The ostomy system according to claim 3, wherein the determination of the operating state is based on a previous operating state and on a deviation of the second value from the second initial value.

6. The ostomy system according to claim 3, wherein the determination of the operating state is based on a time difference between a deviation of the first value from the first initial baseline and a deviation of the second value from the second initial baseline.

7. The ostomy system according to claim 2, wherein the operating state is selected from a plurality of operating states including an operating state indicative of presence of stomal output in an interface between the skin surface and the ostomy appliance and an operating state indicative of presence of sweat in the interface.

8. The ostomy system according to claim 7, wherein, in accordance with at least the absolute difference being in non-compliance with the primary threshold value, the operating state is indicative of presence of stomal output in the interface.

9. The ostomy system according to claim 1, wherein the monitor device further comprises a second interface comprising a transceiver module connected to the processor and configured for connecting the monitor device to an accessory device of the ostomy system.

10. The ostomy system according to claim 9, wherein the monitor device is configured to transmit a primary signal indicative of the operating state.

11. The ostomy system according to claim 1, wherein to determine a first value and a second value comprises applying a voltage across the first sensor and the second sensor and monitoring the associated current, respectively.

12. The ostomy system according to claim 1, wherein the electrical quantity is selected from resistance, impedance and capacitance.

13. An ostomy system, comprising:

an ostomy appliance comprising a sensor assembly, wherein the sensor assembly comprises a stomal opening with a center point and three or more electrodes including a first electrode arranged at a first radial distance from the center point, a second electrode arranged at a second radial distance from the center point, and a third electrode arranged at a third radial distance from the center point, wherein the second radial distance is greater than the first radial distance and the third radial distance is greater than the second radial distance, wherein the first electrode and the second electrode form a primary sensor and wherein the first electrode and the third electrode form a secondary sensor; and a monitor device comprising a processor, a memory connected to the processor, and a first interface connected to the processor and configured for connecting the monitor device to the sensor assembly, and wherein the monitor device is configured to:

determine a first initial baseline of an electrical quantity for the primary sensor and a second initial baseline of the electrical quantity for the secondary sensor in response to a connection between the monitor device and the sensor assembly;

determine a first value of the electrical quantity for the primary sensor and a second value of the electrical quantity for the secondary sensor; and determine an operating state of the ostomy appliance based on at least a previous operating state and a deviation of the second value from the second initial value.

14. The ostomy system according to claim 13, wherein the monitor device is configured to determine the operating state further based on an absolute difference between the first value and the second value.

15. The ostomy system according to claim 14, wherein the absolute difference is compared with a primary threshold value to determine the operating state.

16. The ostomy system according to claim 13, wherein the determination of the operating state is further based on a deviation of the first value from the first initial baseline.

17. The ostomy system according to claim 13, wherein the monitor device further comprises a second interface comprising a transceiver module connected to the processor and configured for connecting the monitor device to an accessory device of the ostomy system.

18. The ostomy system according to claim 17, wherein the monitor device is configured to transmit a primary signal indicative of the operating state.

19. The ostomy system according to claim 13, wherein to determine a first value and a second value comprises applying a voltage across the first sensor and the second sensor and monitoring the associated current, respectively.

20. The ostomy system according to claim 13, wherein the electrical quantity is selected from resistance, impedance and capacitance.

* * * * *